United States Patent [19]

Nevalainen et al.

[11] Patent Number: 5,298,405
[45] Date of Patent: Mar. 29, 1994

[54] ENZYME PREPARATIONS WITH RECOMBINANTLY-ALTERED CELLULOSE PROFILES AND METHODS FOR THEIR PRODUCTION

[75] Inventors: Helena Nevalainen, Espoo; Jonathan Knowles, Helsinki; Pirkko Suominen, Vantaa; Merja Penttilä, Helsinki; Arja Mäntylä, Espoo, all of Finland

[73] Assignee: Alko Limited, Helsinki, Finland

[21] Appl. No.: 524,308

[22] Filed: May 16, 1990

Related U.S. Application Data

[63] Continuation-in-part of Ser. No. 496,155, Mar. 19, 1990, which is a continuation of Ser. No. 44,077, Apr. 29, 1987.

[51] Int. Cl.[5] .................. C12N 15/00; C12N 15/56; C12N 15/80; C12N 15/90
[52] U.S. Cl. .................. 435/209; 435/69.1; 435/172.3; 435/277; 435/278; 435/252.3; 435/200; 435/232; 935/37; 935/61; 935/64; 935/68
[58] Field of Search .......... 435/277, 278, 252.3, 435/69.1, 172.3

[56] References Cited

U.S. PATENT DOCUMENTS

| | | | |
|---|---|---|---|
| 4,713,336 | 12/1987 | Srinivasan et al. | 435/155 |
| 4,745,062 | 5/1988 | Guerineau et al. | 435/209 |
| 4,828,994 | 5/1989 | Fahwestack et al. | 435/172.3 |
| 4,894,338 | 1/1990 | Knowles et al. | 435/172.3 |
| 4,904,599 | 2/1990 | Ozaki et al. | 435/252.33 |

FOREIGN PATENT DOCUMENTS

| | | | |
|---|---|---|---|
| 137280 | 4/1985 | European Pat. Off. | 435/172.1 |
| 244234 | 11/1987 | European Pat. Off. | 435/172.1 |
| 262040 | 3/1988 | European Pat. Off. | 435/277 |
| 334739 | 9/1989 | European Pat. Off. | 435/277 |
| 341947 | 11/1989 | European Pat. Off. | 435/172.1 |
| 30353188 | 1/1990 | European Pat. Off. | 435/69.1 |
| WO85/04672 | 10/1985 | PCT Int'l Appl. | 435/172.1 |
| WO86/01843 | 3/1986 | PCT Int'l Appl. | 435/41 |
| WO89/08738 | 9/1989 | PCT Int'l Appl. | 435/278 |
| 460363B | 10/1989 | Sweden | 435/41 |

OTHER PUBLICATIONS

Kantelinen, A., *Kemia-Kemi* 15:228–231 (1988).
Shoemaker, S. et al., *Bio/Tech.* 1:691–695 (1983).
Teeri, T. T. et al., *Bio/Tech.* 1:696–699 (1983).
PenttiläM. et al., *Gene* 45:253–263 (1986).
Van Arsdell, J. N. V. et al., *Bio/Tech.* 5:60–64 (1987).
Chen, C. M. et al., *Bio/Tech.* 5:274–278 (1987).
Saloheimo, M. et al., *Gene* 63:11–21 (1988).
Saloheimo, M. et al., *Gene* 85:343–351 (1989).
Kirk, T. K. in: *Biochem. & Genetics of Cellulase Degradation,* Aubert et al., FEMS Symp No. 43, Acad. Press, Harcourt, Brace Jovanovitch Publ., London, pp. 315–332 (1988).
Bailey, M. J. et al., *Enz. Microb. Technol.* 12:266–271 (1990).
Nevalainen, H. 1985, Technical Research Center of Finland Publications 26, Espoo, Finland.
Durand, H. et al., in *Biochem and Genetics of Cellulose Degradation,* pp. 131–151 (1987) J-P Aubert et al., eds. Acad. Press, N.Y.
Bailey, M. J. et al., *Enz. Microb. Tech.* 3:153–157 (1981).
Teeri, T. T. et al., *Anal. Biochem.* 164:60–67 (1987).
Penttilä, M. E. et al., *Gene* 63:103–112 (1988).
Teeri, T. T. et al., *Gene* 51:43–52 (1987).
Berse, B. et al., *Gene* 25:109–117 (1983).
Penttilä, M. et al., *Gene* 61:155–164 (1987).
Harkki, A. et al., *Bio/Tech* 7:596–603 (1989).
Sheir-Neiss, G. et al., *Appl. Microb. Biotechnol.* 20:46–53 (1984).

(List continued on next page.)

Primary Examiner—Robert A. Wax
Assistant Examiner—William W. Moore
Attorney, Agent, or Firm—Sterne, Kessler, Goldstein & Fox

[57] ABSTRACT

Enzyme preparations enriched in hemicellulase-, pectin-, and/or lignin-degrading enzymes are described which are also partially or completely deficient in cellulase degrading activity. Such preparations may be utilized in an crude, unpurified form and are especially useful in the production of pulp and paper.

31 Claims, 8 Drawing Sheets

OTHER PUBLICATIONS

Durand, H. et al., Enzyme Microb. Technol. 10:341–346 (1988).

International Search Report, Appl. No. PCT/FI91/00152.

Wallace, L. et al., Biochem. Soc. Symp. 48:87–95 (1083).

Summary page ii, and FIGS. 7a and 7b from "*Trichoderma reesei*-homeen endoglukanaasi I:n tuoton tehostaminen geeniteknisesti", Master of Science Thesis of Taina Karhunen, Feb. 1990.

Nevalainen, H. et al., Chapter 60 in: "Biotechnology In Pulp And Paper Manufacture-Applications And Fundamental Investigations", Proc. of 4th Intl. Conf. on Biotech. in the Pulp and Paper Industry, T. Kent Kirk and Hou-Min Chang, eds. Butterworth-Heinemann, 1990, pp. 593–559.

Text of a Lecture given by Helena Nevalainen at the "Fourth International Conference on Biotechnology in the Paper and Pulp Industry," Raleigh, N.C., USA May 16–19, 1989.

Silva, J. et al., 1988, Journal of Biotechnology 8:249–256.

Hagspiel, K. et al., 1989, Applied Microbiology and Biotechnology 32:61–67.

Knowles, J., et al., 1989, in *Proceedings of Doe EMBO-Alko Workshop on Molecular Biology of Filamentous Fungi*, Nevalanen, H. et al., Eds., pp. 113–118.

Waksman, G. et al., 1989, in *Proceedings of the EMBO-Alko Workshop on Molecular Biology of Filamentous Fungi*, Nevalainca, H. et al., Eds. pp. 197–206.

Bergfors, T., et al., 1989, *Journal of Molecular Biology* 209:167–169.

Nevalainen, H. eds., 1990, Kemiu-Kemi, 17:204–206.

Teeri, T. T., 1987, *The Cellulolytic Enzyme System & Trichoderma Reesei*, Technical Research Center of Finland, 52 pages, Appendix.

Knowles, J., et al., 1988, in Bio Chemistry and Genetics of Cellulose Degradation, Academic Press Limited, pp. 153–169.

Poutaneva, K. et al., 1987, Journal of Biotechnology 6:49–60.

Knowles, J., et al., 1986, Kemia-Kemi, 3:203–206.

Pentillä, M., et al., 1987, in *Industrial Yeast Genetics*, Korhola M., et al., Eds., vol. 5, Foundation for Biotechnical and Industrial Research, pp. 189–197.

El-Gregory, S., et al., 1989, Proceedings, National Academics of Sciences, USA, 86:6138–6141.

Iyayi, C. B., et al., 1989, Archives of Microbiology, 151:326–330.

Knowles, J. K. C. et al., 1987, Trends in Biotechnology, 5:255–261.

Schwarz, W. H., et al., 1986, Applied and Environmental Microbiology 51(6): 1293–1299.

Jansson, C., et al., 1987, Plant Physiology 85:1021–1025.

Saddler, J. N., et al., 1982, Canadian Journal of Microbiology, 28:1311–1319.

Teeri, T. T., et al., 1990, in *Trichoderma reesei Celluloses*, Kubicek, C. P., et al., Eds., Royal Chemistry Society (Britain) pp. 156–167.

ENZYME PREPARATIONS WITH RECOMBINANTLY-ALTERED CELLULOSE PROFILES AND METHODS FOR THEIR PRODUCTION

CROSS REFERENCE TO RELATED APPLICATIONS

This application is a continuation-in-part of U.S. application No. 07/496,155, filed Mar. 19, 1990, which is a continuation of U.S. application No. 07/044,077, filed Apr. 29, 1987.

FIELD OF THE INVENTION

The present invention is related to enzyme preparations with unique enzyme profiles. Methods for the production of such enzyme preparations by genetically engineering members of the species Trichoderma are disclosed. These preparations are especially useful in the pulp and paper industries, and for fodder production.

BACKGROUND OF THE INVENTION

Cellulose is a linear polysaccharide of glucose residues connected by $\beta$-1,4 linkages. In nature, cellulose is usually associated with lignin, other polysaccharides such as pectin, and hemicelluloses such as xylan. These components must be extracted from the cellulose in many instances to form an acceptable commercial pulp or paper product.

In the pulp and paper industry, cellulose pulp obtained by sulphate cooking in particular is brown, mainly because of lignin remaining in the pulp. Lignin is currently removed by bleaching, whereby the pulp is rendered usable for high-quality paper and cardboard products. Unbleached pulp contains 3 to 5 percent residual lignin. This residual lignin may be linked to hemicelluloses with covalent bonds. Residual lignin is traditionally removed in a multi-stage bleaching procedure using a combination of chlorination (the bleaching) and extraction stages.

The effluent from such bleaching plants is a growing environmental concern due to its content of numerous chlorinated substances, including chlorinated phenols and dioxines. Chlorine is further bound to residues of lignin and acids which are still left in the cellulose pulp after completed bleaching. This residual chlorine ends up in the environment, when paper and cardboard products are discarded. There is therefore a great interest in reducing the use of chlorine compounds like pure chlorine gas, chlorine dioxide or sodium or potassium hypochlorite.

The use of purified hemicellulose hydrolyzing enzymes for some processes in pulp and paper processing is known (WO 89/08738, EP 341,947, EP 334,739 and EP 262,040). For biobleaching purposes, the addition of purified hemicellulose hydrolyzing enzymes, by degrading lignin-hemicellulose complexes, may avoid or diminish the use of chlorine compounds in the bleaching processes of cellulose pulp (Kantelinen, *Kemia Kemi* 15(3):228-231 (1988)). Alternatively, or at the same time, pectin and/or lignin may be decomposed with pectin and/or lignin degrading enzymes, respectively. However, the isolation of purified enzymes at levels naturally produced from native sources for use in these processes is timeconsuming, tedious and very expensive on a large scale.

Costs can be lowered by using a conventional (cell homogenate or lysate preparation) crude enzyme preparation which contains a desired enzyme. However, crude preparations of these enzymes are usually obtained from fungal sources and further contain undesired enzymes, for example, cellulases, whose addition is detrimental to the production of the pulp or paper end product.

Consequently, there is a clear demand for enzyme preparations, which contain unique enzyme profiles, tailormade, that is, designed specifically for the purposes of the industry in which they are to be used, and which can be obtained in a cost-effective manner, such as, for example, directly from the culture medium of a microorganism which has been modified so that it produces the desired enzymes, but not appreciable quantities of undesired enzymes.

SUMMARY OF THE INVENTION

Recognizing the importance of eliminating undesirable waste products from wood processing industries, and cognizant of the undesirability of current enzymatic methods of such treatment due to cost or enzymatic contaminant concerns, the inventors have investigated the use of recombinant DNA techniques in the design of hosts which would be useful as a large-scale source of recombinantly produced enzymes of interest to this industry.

These studies have resulted in the development of fungal hosts which express large amounts of desirable enzymes (hemicellulases, pectin degrading enzymes or lignin degrading enzymes).

These studies have also resulted in the development of fungal hosts which not only express large amounts of desirable enzymes (hemicellulases, pectin degrading enzymes or lignin degrading enzymes) but also are deficient in at least one enzymatic component of the cellulase degradation system.

Thus, it is an object of the invention to provide recombinant fungal hosts which are partially or completely deficient in cellulase activity.

It is a further object of the invention to provide fungal hosts which are capable of expressing high levels of hemicellulase activity and/or pectin degrading activity and/or lignin degrading activity in addition to being partially or completely deficient in cellulase activity.

It is an additional object of the invention to provide enzyme compositions which are enriched in said hemicellulase activity and/or pectin degrading activity and/or lignin degrading activity and which are partially or completely deficient in cellulase activity.

DETAILED DESCRIPTION OF THE INVENTION

I. Definitions

Figure 1:
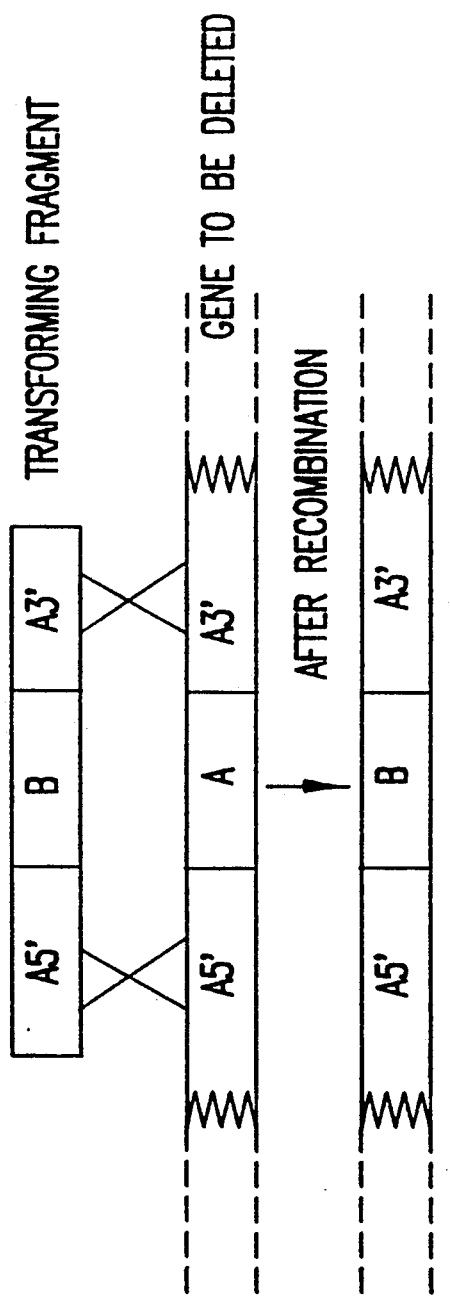
FIG. 1 shows the general strategy for deleting a gene.

In the description that follows, a number of terms used in recombinant DNA (RDNA) technology are extensively utilized. In order to provide a clear and consistent understanding of the specification and claims, including the scope to be given such terms, the following definitions are provided.

Cellulase. Cellulase is a collective term which encompasses enzymes which catalyze reactions which participate in the degradation of insoluble cellulose to soluble carbohydrate. The term "cellulase" is known in the art to refer to such a group of enzymes. For hydrolysis of cellulose to glucose, three cellulase enzymes (three types of cellulase enzyme activity) are needed: randomly cleaving endoglucanases (1,4,-β-D-glucan glucanohydrolase, EC 3.2.1.4) which usually attack substituted soluble substrates and show no activity to crystalline cellulose; cellobiohydrolase (1,4-β-D-glucan cellobiohydrolase, EC 3.2.1.91 which is capable of degrading crystalline cellulose but has no activity towards derivatized cellulose and β-glucosidase (β-D-glucoside glycohydrolase, EC 3.2.1.21) which degrades cellobiose and cello-oligosaccharides to yield glucose. Each of the three main types of enzymes listed above occurs in multiple forms. For example, two immunologically distinctive cellobiohydroloases, CBH I and CBH II are known. In addition, 5-8 electrophoretically distinct endoglucanases are known. Synergistic action between some of these enzymes has been demonstrated. Cellulase activity is synonymous with cellulolytic activity.

The biosynthesis of cellulases is induced by cellulose, cellobiose, sophorose and lactose, and repressed by glucose or other readily utilizable carbon sources.

By a Trichoderma host which is "substantially incapable" of synthesizing one or more cellulase enzymes is meant a Trichoderma host in which the activity of one or more of the cellulase enzymes is depressed, deficient, or absent when compared to the wild-type Trichoderma.

Enzyme Preparation. By "enzyme preparation" is meant a composition containing enzymes which have been extracted from (either partially or completely purified from) fungi. The term "enzyme preparation" is meant to include a composition comprising medium used to culture such fungi and any enzymes which the fungi have secreted into such medium during the culture.

Bio-bleaching. By "bio-bleaching" is meant the extraction of lignin from cellulose pulp by the action of hemicellulose hydrolyzing enzymes and/or lignin degrading enzymes.

Gene. A DNA sequence containing a template for a RNA polymerase. RNA that codes for a protein is termed messenger RNA (mRNA) and, in eukaryotes, is transcribed by RNA polymerase II. However, it is also known to construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA and from which intervening sequences (introns) have been removed.

By an enzyme homologous to a Trichoderma host of the invention is meant that an untransformed Trichoderma of the same species as the host species naturally produces some amount of the native protein; by a gene homologous to a Trichoderma host of the invention is meant a gene found in the genome of an untransformed Trichoderma of the same species as the host species.

By an enzyme heterologous to a Trichoderma host of the invention is meant that an untransformed Trichoderma of the same species as the host species does not naturally produce some amount of the native protein; by a gene heterologous to a Trichoderma host of the invention is meant a gene not found in the genome of an untransformed Trichoderma of the same species as the host species.

Cloning vehicle. A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are tetracycline resistance or ampicillin resistance. The word "vector" is sometimes used for "cloning vehicle." Alternatively, such markers may be provided on a cloning vehicle which is separate from that supplying the gene of interest.

Expression vehicle. A vehicle or vector similar to a cloning vehicle but which is capable of expressing a gene of interest which has been cloned into it, after transformation into a desired host. In a preferred embodiment, such expression vehicle provides for an enhanced expression of a gene of interest which has been cloned into it, after transformation into a desired host.

In a preferred embodiment, the gene of interest which is provided to a fungal host as part of a cloning or expression vehicle integrates into the fungal chromosome. Sequences which derive from the cloning vehicle or expression vehicle may also be integrated with the gene of interest during the integration process.

The gene of interest may preferably be placed under the control of (i.e., operably linked to) certain control sequences such as promoter sequences provided by the vector (which integrate with the gene of interest). If desired, such control sequences may be provided by the fungal host's chromosome as a result of the locus of insertion.

Expression control sequences on an expression vector will vary depending on whether the vector is designed to express a certain gene in a prokaryotic or eukaryotic host (for example, a shuttle vector may provide a gene for selection in bacterial hosts) and may additionally contain transcriptional elements such as, enhancer elements, termination sequences, and/or translational initiation and termination sites.

II. Genetic Engineering of the Trichoderma Hosts

The process for genetically engineering the hosts of the invention is facilitated through the cloning of genetic sequences which are capable of encoding a desired enzymic activity and through the expression of such genetic sequences. As used herein, the term "genetic sequences" is intended to refer to a nucleic acid molecule (preferably DNA). Genetic sequences which are capable of encoding a desired enzyme are derived from a variety of sources. These sources include genomic DNA, cDNA, synthetic DNA, and combinations thereof.

The mesophilic imperfect fungus *Trichoderma reesei* (formerly *T. viride*) is classified as a member of Fungi imperfecti. Fungi imperfecti is a catch-all category of fungi which have no sexual reproduction or obvious affinities with sexually reproducing genera, such as the highly characteristic Aspergillus. Although Trichoderma has been reported to possess a poorly defined sexual stage being an imperfect state of the perfect ascomycete species Hypocrea, the genera Aspergillus and Trichoderma are clearly to be considered taxonomically very different.

The improved enzyme preparations according to this invention are produced by the fungus Trichoderma which has been modified by recombinant DNA techniques. The Trichoderma hosts of the invention are modified so as to be totally deficient in at least one cellulase enzyme (whose activity is undesirable during pulp and paper processing). Thus, although the remaining cellulase activities may be unaffected, the Trichoderma hosts of the invention are partially or completely deficient in the necessary complement of enzymes which will fully degrade cellulose to glucose, and, as a result, such degradation is greatly lowered or completely blocked.

According to this invention, it is also possible to enrich Trichoderma hosts for an enzyme whose activity is desirable for pulp and paper processing purposes by inactivating or eliminating at least one cellulase enzyme. In one embodiment, the cbh1 gene is merely mutated. Since the majority of the secreted proteins of Trichoderma may be the cellulase activity encoded by the gene cbh1, (the cellobiohydrolase, CBHI, protein), by constructing Trichoderma hosts in which the cbh1 gene is mutated to an inactive form, the relative percent of the remaining proteins secreted by Trichoderma in the culture medium may be increased. In another embodiment, a desired gene is inserted preferably into the cbh1 locus such that expression of the desired gene is operably linked to the strong cbh1 promoter. In a highly preferred embodiment, a casette comprising a desired gene already operably linked to the homologous cbh1 promoter is inserted into the cbh1 locus.

The Trichoderma hosts of the invention may be modified to produce an increased amount of one or more enzymes whose activities are useful for pulp and paper processing (either hemicellulase and/or a pectin degrading enzyme, and/or a lignin degrading enzyme). The terms "pectin degrading enzyme" and "lignin degrading enzyme" are meant to include those enzymes which alter or metabolize pectin and lignin (for example, oxidize), respectively, in the host cell.

In the hosts of the invention, any one, some, or all of the cellulolytic enzymes are eliminated, reduced, inactivated, or repressed by methods known in the art so as to result in the host's partial or complete inability to degrade cellulose to glucose. Undesired cellulolytic enzyme activities can be eliminated, reduced, inactivated, or repressed by several methods, e.g., by inactivating the gene(s) encoding such enzyme (for example, by introducing a frame-shift mutation to the gene), by deleting the entire whole gene or large segments of the gene, by replacing the gene with another DNA via homologous recombination, by compensation of the gene region, by additional integration, by double crossing-over, and by transforming the host cell with a genetic construct capable of expressing an antisense RNA directed against the coding sequence for that gene, etc.

For example, inactivation of genes coding for cellulolytic activities may be performed as described in European Patent Applications EP 137,280 and EP 244,234.

Trichoderma fungi produce large amounts of identical, predominantly haploid uninucleate conidia which constitute excellent material for various mutagenic treatments. However, even a haploid mutated nucleus can produce a heterokaryotic colony (mycelium) if a mutation becomes initially fixed only in one of the two strands of the DNA double helix (mosaicism). The amount of mosaic mutants depends on both the mutagen and dose used. In fungi forming haploid uninucleate conidia, the problem of heterokaryotic mycelium can be handled by allowing conidiation and by reisolation of colonies originating from single separate conidia. This cycle can be repeated several times.

Examples of chemical mutagens useful for mutengenizing the Trichoderma hosts of the invention include alkylating agents, such as, for example, N-methyl-N'-nitro-N-nitrosoguanidine (NTG), ethylmethanesulphonate (EMS) and diethylsulphate (DES). Hydroxylamine and chemicals deaminating DNA bases such as nitrous acid are also useful. Ionizing radiation ($\gamma$- and X-rays) as well as ultraviolet irradiation (UV) are examples of physical mutagens useful in Trichoderma strain mutagenesis.

The use of solid media permits rapid screening of thousands of colonies arising from mutagenized conidia for the presence or absence of specific enzymes and allows quantitative estimation of the amount of enzyme produced.

Several types of solid media for detection of enzymes, for example, extracellular amylolytic enzymes, pectinase, protease, chitinase, $\beta$-galactosidase and cellulase, lipase, urease, RNAase and DNAase are known in the art.

Many fungi form large diffuse colonies when grown on solid media. Addition of chemical agents restrictive to colony growth may therefore be desired to allow development of more than one (up to 100) colony per one plate. Among agents used for the purpose are rose bengal, oxgall and phosphon D, Triton X-100 and saponin. With some fungi, replica plating technique analogous to that developed for bacteria can, in certain cases, be used to test the properties of fungal colonies on different growth media.

Screening on plates is usually followed by cultivation of the selected colonies in shake flasks in a liquid production medium for measurement of enzyme activity. The best isolates showing enhanced enzyme production in shake flask scale may be in a second round of mutagen treatment if desired.

Homologous genes which it is desirable to inactivate or delete according to this invention include, for example, the cellulase genes cbh1, cbh2, eg11, eg13 (which encode the proteins cellobiohydrolase I, cellobiohydrolase II, endoglucanase I and endoglucanase II) or combinations of these genes. Eliminating the activity of any of these genes will result in a host which is partially or completely deficient in its ability to degrade cellulose to glucose. Such elimination of cellulolytic activity may be achieved at the genomic level, by eliminating the gene or modifying it into a form which is incapable of expression. Such elimination may also be achieved at the translational level, by hybridizing the mRNA which encodes the protein to an antisense RNA to a degree which prevents the translation of the hybridized RNA.

In a preferred embodiment, a cellulase activity is selectively inactivated so that some, but not all of the cellulase components are inactivated. For example, if it is desired to maintain the host's ability to hydrolyze β-glucan, then the endoglucanase gene would not be inactivated.

The inactivation of, e.g., one of the cellulase genes can be based on transformation of Trichoderma reesei with a plasmid carrying a defected gene as described in patent application EP 244,234. Homologous recombination of the plasmid at the chromosomal cellulase gene locus causes insertional inactivation of the endogenous T. reesei, cellulase gene. The plasmid used for transformation contains only part of the cellulase coding region and produces inactive protein. No 5' flanking sequences are included. A frameshift mutation can also be introduced to the truncated coding region. A selection marker, (for example amdS (acetamidase) or argB (ornithine carbamoyl transferase)) or a marker for screening (for example, lacZ) can be coupled to the plasmid used for the transformation or the transformation can be done as a cotransformation, which means that the selectable marker and the defected gene are on different plasmids (EP 244,234). Inactivation of a gene with homologous recombination may be done with a circular DNA, which integrates in a colinear manner into the Trichoderma chromosomal DNA.

The deletion of an undesired gene can be done by using a strategy the principle of which is described in FIG. 1. The recipient strain is transformed with a linear DNA fragment containing a selectable marker gene (like trpC, argB or amdS) and/or a foreign desired gene of interest which is to be expressed, flanked by the 5' and 3' flanking regions of the gene to be deleted. Homologous recombination at the A locus will thus lead to replacement of the A gene with the selection marker and/or desired gene B. If the 5' region in the transforming fragment is taken upstream from the promoter area, the promoter will also be removed in the resulting replacement strain. Gene A can be any Trichoderma gene, preferably a cellulase gene, the flanking regions of which can be cloned/isolated. Moreover the linear DNA fragment can be ligated to form a circular plasmid or in addition the circular form may contain DNA needed for replication in bacteria (e.g., in E. coli). The linear DNA fragments used in deletion of undesired genes can be constructed for example from pUC19 plasmids (Yanisch Perron et al., Gene 33:103-119 (1985)).

This method is described in more detail in the Example 1B which describes the deletion of cbh2 gene from the genome of Trichoderma by said method.

Clones of the cellulase enzymes have been described which may be used to design mutant sequences for inactivation of homologous sequences in the hosts of the invention. Any mutant sequence which results in the inactivation of the enzyme's activity may be used. For example, the gene for the native cellobiohydrolase CBH I sequence has been cloned by Shoemaker et al. (Shoemaker, S., et al., Bio/Technology 1:691-695 (1983)) and Teeri et al. (Teeri, T., et al., Bio/Technology 1:696-699 (1983)) and the entire nucleotide sequence of the gene is known (Shoemaker, S., et al., Bio/Technology 1:691-696 (1983)). From T. reesei, the gene for the major endoglucanase (EG I) has also been cloned and characterized (Penttilä, M., et al., Gene 45:253-263 (1986); Patent Application EP 137,280. Van Arstel, J.N.V., et al., Bio/Technology 5:60-64). Other isolated cellulase genes are cbh2 (Patent Application WO 85/04672; Chen, C.M., et al., Bio/Technology 5:274-278 (1987)) and eg13 (Saloheimo, M., et al., Gene 63:11-21 (1988)).

In another embodiment, the Trichoderma hosts of the invention which are partially or completely deficient in at least one cellulase activity are further transformed with a genetic construct capable of expressing at least one desired pulp and paper processing enzyme which is homologous to Trichoderma, so as to provide for increased amounts of this enzyme in the Trichoderma host. Examples of desired pulp and paper processing homologous enzymes include, for example, hemicellulases and pectin-degrading enzymes. Trichoderma is inherently capable of producing a variety of hemicellulases including endoxylanases, β-xylosidase, α-arabinosidase, α-D-glucuronidase and acetyl esterase, the activity of any of which may be a desired enzyme in the enzyme preparations of the invention. Also, native Trichoderma produces minor amounts of pectin degrading enzymes like polygalacturonase which may be classified as a desired enzyme in the enzyme preparations of the invention. Further, any other Trichoderma enzyme which oxidizes cellulose may be utilized in the enzyme preparations of the invention and may be a desired enzyme.

Comparison with xylanolytic enzymes produced by Trichoderma reesei QM 9414, Aspergillus awamori VTT-D-75028, Fusarium oxysporum VTT-D-80134, Bacillus subtillis ATCC 12711 and Streptomyces olivochromogenes ATCC 21713 has shown that the highest xylanase activity was produced by T. reesei. Therefore, under conditions where it is desired to retain xylanase activity, T. reesei is an advantageous host.

Further, although the above preparations from the different microbial origins differed with respect to β-xylosidase activity and side-group cleaving activities, the T. reesei culture filtrate contained all the side-group cleaving activities assayed (acetyl esterase, α-glucuronidase and α-arabinosidase) whereas those from F. oxysporum and S. olivochromogenes only contained esterase. Thus Trichoderma is also advantageous as a host because it naturally produces a wide spectrum of xylanolytic enzymes the proportions of which can be manipulated by genetic engineering for different applications to provide enzyme preparations tailored for those purposes.

According to this invention, the genetic constructs which encode homologous enzymes which are desirable for pulp and paper processing purposes may be introduced into the genome of Trichoderma and enhanced expression can also be achieved by using strong promoters such as cbh1 and, if desired, additional or modified regulatory regions, such as, for example, enhancer sequences. Preferably, such regulatory sequences are homologous to Trichoderma. A regulatory region, and especially a promoter, may be modified to contain only those sequence elements needed for expression and/or to retain a region which is responsible for high expression levels. Enhancer sequences may be introduced concurrently with the gene of interest as a separate DNA element but operably-linked to such gene of interest, for example, as a DNA sequence which is colinear with that providing the gene of interest (for example, in a 5' or 3' non-translating sequence, or in an intron).

In a highly preferred embodiment, the homologous gene introduced to the genome of Trichoderma is a gene encoding a homologous hemicellulase and/or a homologous pectin-degrading enzyme.

In another highly preferred embodiment, a heterologous gene is introduced in addition to a homologous gene. Such an embodiment is useful when Trichoderma does not naturally produce a desired activity.

In some applications, although one cellulolytic activity may be eliminated, reduced, inactivated, or repressed, it may be desirable to introduce a gene encoding a different cellulolytic enzyme into the host cells so as to enhance one specific cellulolytic activity. For example, in the production of microcrystal cellulose the amorphous portions of cellulose should be hydrolyzed, but the polymeric structure should not be degraded. This can be done with an enzyme preparation comprising an elevated amount of endoglucanase I capable of hydrolyzing amorphous portions of cellulose. Thus, in those preparations in which such hydrolysis is desired, a host which expresses elevated levels of endoglucanase I may be used.

In another embodiment, the Trichoderma host which already expresses a homologous form of an enzyme is transformed with a genetic construct encoding a heterologous form of the same enzyme. In a further embodiment, a Trichoderma host which does not express a certain enzyme is transformed with one or more genetic constructs encoding enzyme(s) heterologous to Trichoderma.

According to this invention increased amounts of a heterologous enzyme whose activity is desired for pulp and paper processing purposes are achieved by introducing the gene producing such heterologous desired enzyme into a specific locus and/or introducing the gene in multicopies into the genome of Trichoderma as described above.

In a preferred embodiment, the gene encoding a desired enzyme is inserted into the cbh1 locus such that it is operably linked to the strong cbh1 promoter. As described below, enhanced production is achieved by using strong promoters such as cbh1. Increased amounts of the desired heterologous enzyme are also achieved when Trichoderma's cellulase producing capacity is lowered in general, even if the heterologous gene is not inserted into the cbh1 locus.

In one embodiment, the heterologous gene to be introduced to the genome of Trichoderma is a gene encoding an enzyme capable of lignin polymer degradation, for example lignin peroxidase LIII from *Phlebia radiata* (Saloheimo et al., *Gene* 85:343–351 (1989)), or the gene for some other ligninase, laccase or Mn peroxidase (Kirk, In: *Biochemistry and Genetics of Cellulose Degradation*, Aubert et al. (eds.), FEMS Symposium No. 43, Academic Press, Harcourt, Brace Jovanovitch Publishers, London. pp. 315–332 (1988)). When it is desired to reduce residual lignin which is present in unbleached cellulose pulp, an enzyme preparation of the invention which contains high levels of hemicellulases and lignin degrading enzymes and low levels of cellulolytic enzymes is useful.

In another embodiment, the heterologous gene to be introduced to the genome of Trichoderma is a gene encoding an enzyme capable of pectin degradation, such as, for example, endo-polygalacturonase, exo-polygalacturonase, pectinesterase or pectin and pectin acid lyase. Pectinases are naturally found in two main sources: in plants and in fungi. Much of the industrially significant work has been carried out with fungi of the genus Aspergillus (Bailey and Pessa, *Enzyme Microb. Technol.* 12:266–271 (1990)).

A gene encoding a desired enzyme, either homologous or heterologous, such as a hemicellulose hydrolyzing, or a pectin or a lignin degrading enzyme, can be integrated into the genome of Trichoderma by inserting the gene into a general expression vector, for example, pAMHI10, which is described in the patent application EP 244,234. pAMH110 is derived from pUC19 (Janisch-Perron et al., *Gene* 33:103–119 (1985)) and includes the promoter and terminator of the cbh1 gene and a stuffer fragment between the promoter and terminator sequences which can be removed by digestion with SacII and NdeI. After the ends are made blunt, any DNA, cDNA or chromosomal DNA can be inserted between the promoter and terminator. The desired gene can be inserted to the cbh1 expression cassette in the plasmid pAMH110 between the cbh1 promoter and terminator.

Transcriptional regulatory elements of other genes may be used where it is desired not to use the cbh1 elements. For example a vector construction comprising the 3-phosphoglycerate kinase gene (pgk) transcriptional regulatory regions may be used as 3-phosphoglycerate kinase, a key enzyme for ATP generation by glycolysis, is expressed in the presence of glucose under which conditions the synthesis of cellulases is repressed.

While the inventors do not intend to be bound by any particular theory, the effectiveness of the expression of the desired gene seems to be dependent both on the number of copies of the desired gene integrated to the genome of Trichoderma and on the location of integration of the gene in the genome. In a preferred embodiment, the integration of a desired gene is directed into a specific locus. The use of a linear DNA helps in directing the integration into a homologous locus. In a highly preferred embodiment, the integration of a desired gene is directed into the Trichoderma cbh1 locus.

The DNA constructions prepared according to this invention can be used to transform any Trichoderma strain. Such strains include, for example, *T. reesei* strains QM9414 (ATCC 26921), RUT-C-30 (ATCC 56765), and highly productive mutants like VTT-D-79125, which is a descendant of QM9414 (Nevalainen 1985, Technical Research Centre of Finland Publications 26, (1985), Espoo, Finland). The transformation of Trichoderma may be performed by any technique known in the art and especially by the technique taught in U.S. application Ser. No. 07/044,077, filed Apr. 29, 1987, now abandoned, fully incorporated herein by reference.

The Trichoderma host cells may be cultivated and the desired enzymes produced by cultivating the host strain having the desired properties under any conditions which allow expressing of the desired enzymes. For example, a Trichoderma host strain having the desired properties may be cultivated in a liquid cultivation medium, which may comprise, for example, 6% Solka Floc cellulose, 3% distiller's spent grain, 0.5% $KH_2PO_4$, 0.5% $(NH_4)_2SO_4$, 0.1% struktol . Trichoderma strains are sensitive to glucose repression and require an inducer such as, for example, cellulose, lactose or sophorose (Allen et al., *Biotechnology and Bioengineering* 33:650-656 (1989)). The pH in Trichoderma cultivation should be kept at approximately pH 5 by the addition of phosphoric acid or ammonia and the temperature may be kept at 30° C. during the cultivation. However, the temperature should be adjusted according to the strain and according to the enzyme preparation to be produced (Merivuori et al., *Biotechnology Lett.* 12:117-120 (1990)).

Vector systems may be used in the method of producing Trichoderma hosts for the production of the enzyme preparations of the invention. One element provided by such vector construction may encode the sequence of at least one homologous gene the activity of which it is desired to eliminate, reduce, inactivate, delete or repress. Such vector construction (a) may further provide a separate vector construction (b) which encodes at least one desired gene to be integrated to the genome of Trichoderma and (c) a selectable marker coupled to (a) or (b). Alternatively, a separate vector may be used.

The cloned DNA which is used in the hosts of the invention may or may not include naturally occurring introns. Moreover, such genomic DNA may be obtained in association with the native 5' promoter region of the DNA genetic sequences and/or with the 3' transcriptional termination region if such sequences are capable of functioning in Trichoderma. Further, such genomic DNA may be obtained in association with the genetic sequences which encode the 5' non-translated region of the mRNA and/or with the genetic sequences which encode the 3' non-translated region. To the extent that the Trichoderma host cell can recognize the transcriptional and/or translational regulatory signals associated with the expression of the mRNA and protein, then the 5' and/or 3' non-transcribed regions of the native gene, and/or, the 5' and/or 3' nontranslated regions of the mRNA, may be retained and employed for transcriptional and translational regulation. Genomic DNA can be extracted by means well known in the art (for example, see *Guide to Molecular Cloning Techniques*, S.L. Berger et al., eds., Academic Press (1987)). Alternatively, mRNA can be isolated from any cell which produces or expresses the desired protein, and used to produce cDNA by means well known in the art (for example, see *Guide to Molecular Cloning Techniques*, S.L. Berger et al., eds., Academic Press (1987)). Preferably, the mRNA preparation used will be enriched in mRNA coding for a desired protein, either naturally, by isolation from a cells which are producing large amounts of the protein, or in vitro, by techniques commonly used to enrich mRNA preparations for specific sequences, such as sucrose gradient centrifugation, or both.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding a desired protein may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

Libraries containing clones encoding a desired protein may be screened and a clone to the desired protein identified by any means which specifically selects for that protein's DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for the proteins desired in this invention which can be used to identify clones to such protein can be designed from knowledge of the amino acid sequence of the protein.

Because the genetic code is degenerate, more than one codon may be used to encode a particular amino acid (Watson, J.D., In: *Molecular Biology of the Gene*, 3rd Ed., W.A. Benjamin, Inc., Menlo Park, Calif. (1977), pp. 356-357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J.D., In: *Molecular Biology of the Gene*, 3rd Ed., W.A. Benjamin, Inc., Menlo Park, Calif. (1977)), one or more different oligonucleotides can be identified from the amino acid sequence, each of which would be capable of encoding the protein. The probability that a particular oligonucleotide will, in fact, constitute the actual protein's sequence can be estimated by considering abnormal base pairing relationships and the frequency with which a particular codon is actually used (to encode a particular amino acid) in eukaryotic cells. Such "codon usage rules" are disclosed by Lathe, R., et al. *J. Molec. Biol.* 183:1-12 (1985). Using the "codon usage rules" of Lathe, a single oligonucleotide sequence, or a set of oligonucleotide sequences, that contain a theoretical "most probable" nucleotide sequence capable of encoding the protein's sequence is identified.

The suitable oligonucleotide, or set of oligonucleotides, which is capable of encoding a fragment of the protein's gene (or which is complementary to such an oligonucleotide, or set of oligonucleotides) may be synthesized by means well known in the art (see, for example, *Synthesis and Application of DNA and RNA*, S.A. Narang, ed., 1987, Academic Press, San Diego, Calif.) and employed as a probe to identify and isolate the desired cloned gene by techniques known in the art. Techniques of nucleic acid hybridization and clone identification are disclosed by Maniatis, T., et al. (In: *Molecular Cloning, A Laboratory Manual*, Cold Spring Harbor Laboratories, Cold Spring Harbor, N.Y. (1982)), and by Hames, B.D., et al. (In: *Nucleic Acid Hybridization, A Practical Approach*, IRL Press, Washington, DC (1985)). Those members of the above-described gene library which are found to be capable of such hybridization are then analyzed to determine the extent and nature of the desired genomic coding sequences which they contain.

To facilitate the detection of the desired DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P.J.W., et al., *J. Mol. Biol.* 113:237 (1977) and by T4 DNA polymerase replacement synthesis as described in, for example, Deen, K.C., et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary, J.J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

Thus, in summary, the actual identification of protein's sequence (or a partial sequence of the protein) permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the protein's gene.

In an alternative way of cloning a gene, a library is prepared using an expression vector, by cloning DNA or, more preferably cDNA prepared from a cell capable of expressing a desired protein, into an expression vector. The library is then screened for members which express the protein, for example, by screening the library with antibodies to the protein.

The above discussed methods are, therefore, capable of identifying genetic sequences which are capable of encoding a desired protein or fragments of this protein. In order to further characterize such genetic sequences, and, in order to produce the recombinant protein, it is desirable to express the proteins which these sequences encode. Such expression identifies those clones which express proteins possessing characteristics of the desired protein. Such characteristics may include the ability to specifically bind antibodies directed against the protein, the ability to elicit the production of antibody which are capable of binding the protein, and the ability to provide a protein specific function to a recipient cell, among others.

The cloned protein encoding sequences, obtained through the methods described above, and preferably in a double-stranded form, may be operably linked to sequences controlling transcriptional expression in an expression vector, and introduced into a Trichoderma host cell to produce recombinant protein or a functional derivative thereof. Depending upon which strand of the protein encoding sequence is operably linked to the sequences controlling transcriptional expression, it is also possible to express an antisense RNA or a functional derivative thereof.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively.

Expression of the protein in the Trichoderma hosts requires the use of regulatory regions functional in such hosts. A wide variety of transcriptional and translational regulatory sequences can be employed, since Trichoderma generally recognize eukaryotic host transcriptional controls, such as, for example, those of other filamentous fungi. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

In a preferred embodiment, a desired protein is secreted into the surrounding medium due to the presence of a homologous Trichoderma secretion signal sequence. If a desired protein does not possess its own signal sequence, or if such signal sequence does not function well in Trichoderma, then the protein's coding sequence may be operably linked to a signal sequence homologous or heterologous to Trichoderma. The desired coding sequence may be linked to any signal sequence which will allow secretion of the protein from a Trichoderma host, for example, the signal sequence of the Trichoderma cellobiohydrolase I protein. Such signal sequences may be designed with or without specific protease sites such that the signal peptide sequence is amenable to subsequent removal.

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., substrate or metabolite regulation. Also of interest are constructs wherein both (a) a desired protein's mRNA and (b) antisense RNA directed to a cellulase enzyme are provided in a transcribable forms such that expression of the desired protein's mRNA is accompanied by antisense RNA repression of the expression of one of the host's cellulase enzymes.

Translational signals are not necessary when it is desired to express antisense RNA sequences.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells.

The vectors of the invention may further comprise other operably linked regulatory elements such as enhancer sequences.

In a preferred embodiment, genetically stable transformants of Trichoderma are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

The DNA encoding sequences, obtained through the methods above, will provide sequences which by definition, encode a desired protein and which may then be used to obtain a desired protein's antisense RNA genetic sequences as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of an antisense RNA in the transformed cell. Antisense RNA and its expression may be used to interact with an endogenous DNA or RNA in a manner which inhibits or represses transcription or translation of the gene in a highly specific manner. Use of antisense RNA probes to block gene expression is discussed in Lichtenstein, C., *Nature* 333:801–802 (1988).

Trichoderma is an especially useful and practical host for the synthesis of the enzyme preparations of the invention because Trichoderma is capable of secreting protein at large amounts, for example, concentrations as much as 40 g/L culture fluid have been reported; the homologous Trichoderma cbh1 promoter provides a very convenient promoter for expression of genes-of-interest because is a strong, single copy promoter which normally directs the synthesis of up to 60% of the secreted protein from the Trichoderma host; the transformation system is highly versatile and can be adapted for any gene of interest; the Trichoderma host provides an "animal cell type" high mannose glycosylation pattern; and culture of Trichoderma is supported by previous extensive experience in industrial scale fermentation techniques.

III. Construction and Identification of Antibodies

In the following description, reference will be made to various methodologies well-known to those skilled in the art of immunology. Standard reference works setting forth the general principles of immunology include the work of Catty, D. (*Antibodies, A Practical Approach*, Vol. 1, IRL Press, Washington, D.C. (1988)); Klein, J. (*Immunology: The Science of Self-Nonself Discrimination*, John Wiley & Sons, New York (1982)); Kennett, R., et al. (*Monoclonal Antibodies, Hybridoma: A New Dimension in Biological Analyses*, Plenum Press, New York (1980)); Campbell, A. ("Monoclonal Antibody Technology," In: *Laboratory Techniques in Biochemistry and Molecular Biology*, Volume 13 (Burdon, R., et al., eds.), Elsevier, Amsterdam (1984)); and Eisen, H.N., (In: *Microbiology*, 3rd Ed. (Davis, B.D., et al., Harper & Row, Philadelphia (1980))).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

The antibodies of the present invention are prepared by any of a variety of methods. For example, cells expressing a desired protein, or an antigenic fragment thereof, can be administered to an animal in order to induce the production of sera containing polyclonal antibodies that are capable of specifically binding the protein. In another method, a peptide core protein fragment is chemically synthesized and purified by HPLC to render it substantially free of contaminants. Such a preparation is then introduced into an animal in order to produce polyclonal antisera of high specific activity.

Monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563-681 (1981)). In general, such procedures involve immunizing an animal with the desired protein. The splenocytes of such animals are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands, J.R., et al., *Gastroenterology* 80:225-232 (1981), which reference is herein incorporated by reference. The hybridoma cells obtained through such a selection are then assayed to identify clones which secrete antibodies capable of binding the desired protein.

Through application of the above-described methods, additional cell lines capable of producing antibodies which recognize epitopes of a desired protein can be obtained.

Antibodies against both highly conserved and poorly conserved regions of a protein are useful for identification of clones which encode the genetic sequence of such proteins.

IV. The Enzyme Preparation

According to the invention, there is also provided a method for producing an enzyme preparation partially or completely deficient in cellulolytic activity (that is, in the ability to completely degrade cellulose to glucose) and enriched in enzymes desirable for pulp and paper processing (hemicelluloses and/or pectin degrading enzymes and/or lignin degrading enzymes). By "deficient in cellulolytic activity" is meant a reduced, lowered, depressed, or repressed capacity to degrade cellulose to glucose. Such preparations may be obtained directly from the hosts of the invention. Further, if desired activities are present in more than one recombinant host, such preparations may be isolated from the appropriate hosts and combined prior to use in the method of the invention.

It is envisioned that enzyme preparation which are enriched or partially or completely deficient in specific enzymatic activities will be provided so as to satisfy the requirements of a specific utility in various applications in the pulp and paper industry and in fodder production. Enzyme activities may be added or deleted as described above to provide, remove or retain or lower a desired activity. For example, if the intended application is improvement of the strength of the mechanical mass of the pulp, then the enzyme preparation of the invention may provide enzymes which enhance or facilitate the ability of cellulose fibers to bind together. In a similar manner, in the application of pulp milling, the enzyme preparation of the invention may provide enzymes which enhance or facilitate such swelling. In the preparation of chemically modified cellulose, the enzyme preparation of the invention may provide enzymes which enhance or facilitate the 'softening' of the crystalline portions. In the preparation of microcrystalline cellulose, the enzyme preparation of the invention may provide enzymes which enhance or facilitate the hydrolysis of the amorphous portions of the cellulose.

To obtain the enzyme preparations of the invention, the recombinant hosts described above having the desired properties (that is, hosts substantially incapable of expressing one or more cellulase enzymes and capable of expressing the desired enzymes) are cultivated under suitable conditions, the desired enzymes are secreted from the Trichoderma hosts and into the culture medium, and the enzyme preparation is recovered from said culture medium by methods known in the art.

The enzyme preparation can be produced by cultivating the Trichoderma strain in a fermentor having the desired properties for example in a liquid cultivation medium, which may comprise for example 6% Solka Floc cellulose (BW40, James River Corporation, Hackensack, N.J.), 3% distiller's spent grain (waste after alcohol distillation, ALKO, Ltd., Koskenkorva, Finland), 0.5% KH$_2$PO$_4$, 0.5% (NH$_4$)$_2$SO$_4$, and 0.1% struktol as an antifoaming agent (struktol SB 2023, Schill & Seilacher, Hamburg, FRG). Trichoderma strains are sensitive to glucose repression and require an inducer (cellulose, lactose or sophorose) (Allen et al., *Biotechnology and Bioengineering* 33:650-656 (1989)). The pH should preferably be kept at approximately pH 5 by the addition of phosphoric acid or ammonia and the temperature at 30° C. during the cultivation. However, the temperature may be adjusted according to the strain and according to the enzyme preparation to be produced (Merivuori et al., *Biotechnology Letters* 12(2):117-120 (1990)).

The enzyme preparation is recovered from the culture medium by using methods well known in the art. However, because the hosts of the invention are partially or completely deficient in cellulase activity, it is an advantage of the invention that the enzyme preparations of the invention may be utilized directly from the culture medium with no further purification. If desired, such preparations maybe lyophilized or the enzymatic activity otherwise concentrated and/or stabilized for storage. The enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the Trichoderma hosts.

If desired, an expressed protein may be further purified in accordance with conventional conditions, such as extraction, precipitation, chromatography, affinity chromatography, electrophoresis, or the like.

The Trichoderma and enzyme preparations of the invention have further application in water treatment industries and in fodder production. For example, fodder treated with the enzyme preparations of the invention would be of great food benefit to farm animals because it would be easier for them to digest.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

MATERIALS AND METHODS

Transformation of T. reesei

Transformation of *T. reesei* and selection of AmdS+ and ArgB+ transformants were carried out as described by Penttilä et al., *Gene* 61:155-164 (1987).

Phleomycin resistant transformants were screened as described by Durand et al. in: Biochemistry and Genetics of Cellulose Degradation, p. 135-151, 1987, J.-P. Aubert, P. Beguin and J. Millet (eds.), Academic Press, New York.

In cotransformation with p3SR2 and pAMH111, equal molar amounts of plasmid DNA (5-10 μg) were used. In transformations conferring phleomycin resistance, the relative amounts of plasmid DNA used were 1:1 or 2:1 for pAMH111 and pAN8-1 respectively. When cotransformation was carried out using p3SR2 and pMS4, the plasmid pMS4 was added in 3-4 times molar excess. Transformants were purified through conidia; that is, the conidial suspension was plated again on the selective medium so that every colony started from a single conidia.

In transformations with a linear DNA fragment, the amount of DNA used varied from 2 to 5 μg. The selection marker (amdS (acetamidase) or argB (ornithine carbamoyl transferase, OTCase, E.C. 2.1.3.3)) was within the transforming fragment.

Isolation and Analysis of DNA

Plasmid DNA from E. coli was isolated using standard methods (Maniatis et al. 1982, *Molecular cloning: A Laboratory manual*, Cold Spring Harbor Laboratory. Cold Spring Harbor, N.Y.). Chromosomal DNA was isolated from *T. reesei* using the method of Raeder and Broda, *Lett. Appl. Microbiol.* 1:17-20 (1985)). Southern and Northern hybridizations were performed by standard techniques (Maniatis et al. supra, 1982). Western blotting was carried out according to Maniatis et al., supra, 1982) .

Liguid Cultivation Media and Conditions for Trichoderma

All Trichoderma liquid cultures were started from conidiospores grown on potato dextrose agar as described by Bailey and Nevalainen, *Enzyme Microb. Technol.* 3:153-157 (1981)). Liquid cultivations in shake flasks were performed according to Bailey and Nevalainen, *Enzyme Microb. Technol.* 3:153-157 (1981), except that Finnfloc was replaced with Solca Floc cellulose. Medium used in fermenter cultivations contained 6% Solka Floc cellulose, 3% distiller's spent grain, 0.5% $KH_2PO_4$, 0.5% $(NH_4)_2SO_4$ and 0.1% struktol. The pH was kept between 4.0 and 4.8 by addition of phosphoric acid or ammonia. Fermentations were carried out at 30° C. Maximum yield of enzymes was obtained in 5 days in laboratory fermentations and in 4 days in 100 liter fermenter scale.

Enzyme Assays

All assays for enzyme activity were carried out from culture supernatant fractions after removing the mycelia by centrifugation for 20 min at 3000 rpm. Endoglucanase activity using hydroxyethylcellulose as substrate (HEC, mittelviskös, Fluka AG 54290, pract. grade) and xylanase activity using Sigma X-0376 xylan as substrate, were measured as described by Bailey and Nevalainen, *Enzyme Microb. Technol.* 3:153-157 (1981). Soluble protein was assayed with the method of Lowry et al., *J. Biol. Chem.* 193:265-275 (1951)) using bovine serum albumin as the standard. Cellobiohydrolase activity against filter paper (filter paper unit, FPU) was measured by using the assay developed by Mandels et al., In: *Biotechnol. Bioeng. Symp.* no. 6, p. 21-33, Gaden, E.L., Mandels, M.H., Reese, E.T. and Spano, L.A. (eds.). John Wiley and Sons, New York, (1976).

ELISA Assay for Endoglucanase I

Endoglucanase I protein concentration in the culture supernatant fractions was determined by a double antibody sandwich ELISA. The assays were performed in 96-well flat bottomed microtiter plates at 37° C. (except were noted). Each step was terminated by washing 3 times with phosphate buffered saline pH 7.2 containing 0.05% Tween 20 and 0.02% sodium azide (PBS/Tween).

The plates were coated with mouse monoclonal antibodies directed against endoglucanase I (anti-EGI antibody EI-2) overnight at 4° C. Unoccupied sites on the plastic surface were blocked with 1% BSA in PBS/Tween for 1 hr. Appropriate dilutions of culture supernatant fractions and purified endoglucanase I were then added and incubated for 2 hrs followed by an incubation with rabbit polyclonal antibodies against endoglucanase I for 2 hrs. Bound rabbit antibodies were detected by incubation with swine polyclonal antibodies against rabbit IgG conjugated to alkaline phosphatase (Orion Diagnostics, Espoo, Finland) for 2 hrs. In an end step p-nitrophenylphosphate (1 mg/ml) was added and the reaction stopped after 30 min at room temperature with 2 N NAOH. The developed yellow color was measured photometrically at 405 nm. The concentration of endoglucanase I in culture supernatant fractions was then calculated by comparing their $OD_{405}$ values with a standard dilution curve prepared using purified endolgucanase I and performed at the same time on the same plate.

Fractionation of the Culture Supernatant Fraction by Chromatofocusing

The chromatographic system consisted of a Pharmacia FPLC apparatus equipped with a Mono P HR 5/20 column for chromatofocusing. The resin was stabilized in 25 mM Bistris-HCl buffer, pH 6.5. The crude enzyme mixture produced by *T. reesei* in shake flask culture was diluted with the same buffer to 1 mg/ml protein content. 500 μl enzyme samples were injected into the column and eluted with Pharmalyte/Polybuffer (Pharmacia, 1 ml Pharmalyte$^R$ 2.5–5 ml Polybuffer TM PB 74 in a total 100 ml, adjusted pH to 3.0 with HCl) with pH gradient from 6.5 to 3.0. The flow rate was 30 ml/h. Column effluents were collected in 600 μl fractions and the pH and EGI activity were assayed.

EXAMPLE 1

A. Inactivation of the Major Cellulose cbh1 Gene

The cbh1 gene which encodes the major cellulase in *T. reesei* was inactivated by homologous recombination with plasmid pMS4 containing a 0.8 kb internal fragment of the cbh1 cDNA bearing a frame shift mutation. The pMS4 plasmid was prepared on the following way: the plasmid pTTc01 (Teeri et.al., *Anal. Biochem.* 164:60–67 (1987); Penttilä et al., Gene 63:103–112 (1988)), which contains the full length cDNA clone of the cbh1 gene in the pUC8 vector (Vieira and Messing, Gene 19:259–268 (1982)), was digested with BglI cutting in the signal sequence (Shoemaker et al., *Bio/Technology* 1:691–695 (1983)) and with BglII. The resulting 0.8 kb DNA fragment bearing the 5' region of the cbh1 cDNA was made blunt-ended with S₁ nuclease and was ligated to an EcoRI cut, blunt-ended pUC18 vector (Janesch Perron et al., Gene 33:103–119 (1985)). The clone obtained was cut in the middle of the cbh1 fragment with EcoRI. The EcoRI generated termini were then filled in and back-ligated. The resulting plasmid pMS4 thus contains a frameshift mutation in the middle of the truncated cbh1 cDNA fragment.

*T. reesei* VTT-D-79125 (Bailey and Nevalainen, *Enzyme Microb. Technol.* 3:153–157 (1981)) was cotransformed with pMS4 and p3SR2. p3SR2 carries a 5 kb DNA fragment containing the *A. nidulans* amdS gene cloned into pBR322 (Kelly and Hynes, *EMBO J.* 4:475–479 (1985)). Transformants were selected on the basis of the AmdS+ phenotype after which they were purified from conidia. About 600 clones from 200 independent transformants were then grown on microtiter plates and their cellulase phenotype was tested by the Ouchterlony immunodiffusion (Ouchterlony, *Progr. Allergy* 5:1–78 (1958)) using undiluted growth medium and the CBHI specific sheep antiserum.

Figure 2:
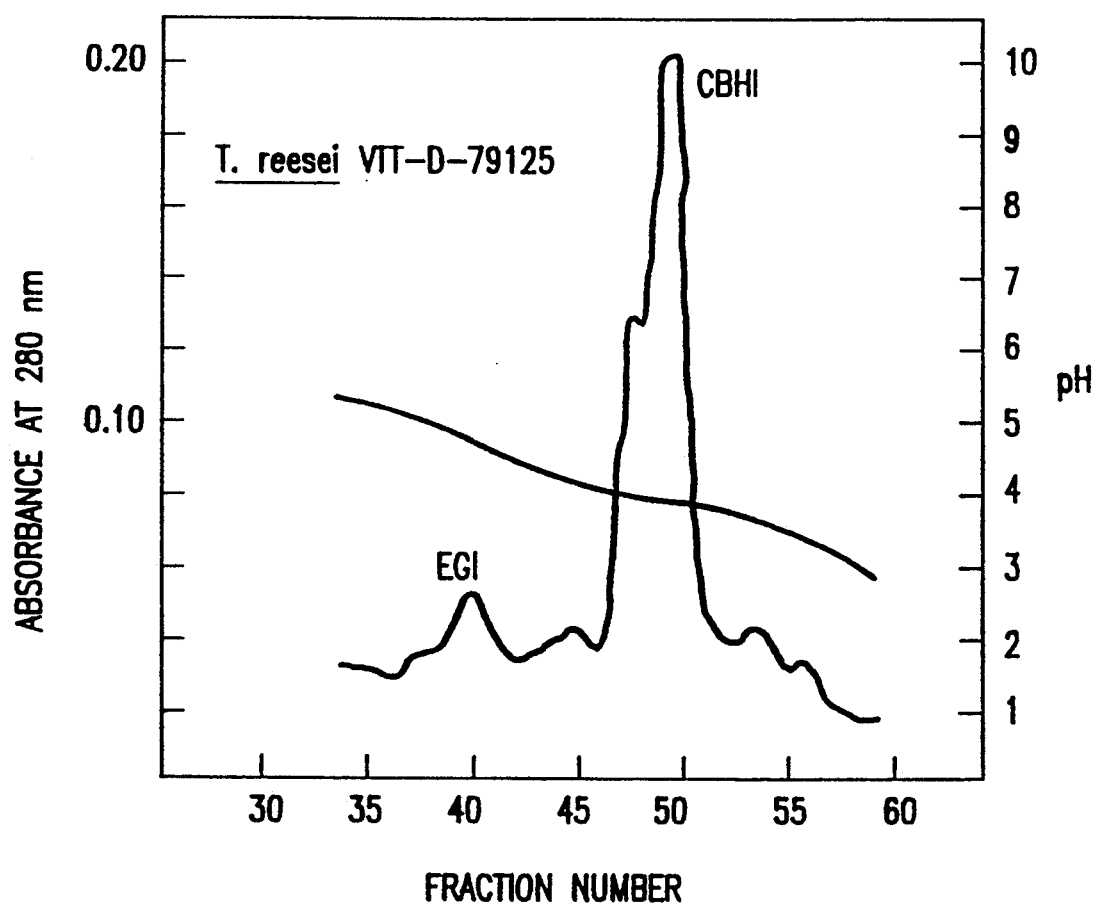
FIG. 2 and FIG. 2A shows an FPLC analysis of the CBHI negative transformant VTT-D-87312 (FIG. 2A) and its comparison to the untransformed host (FIG. 2).
Figure 2A:
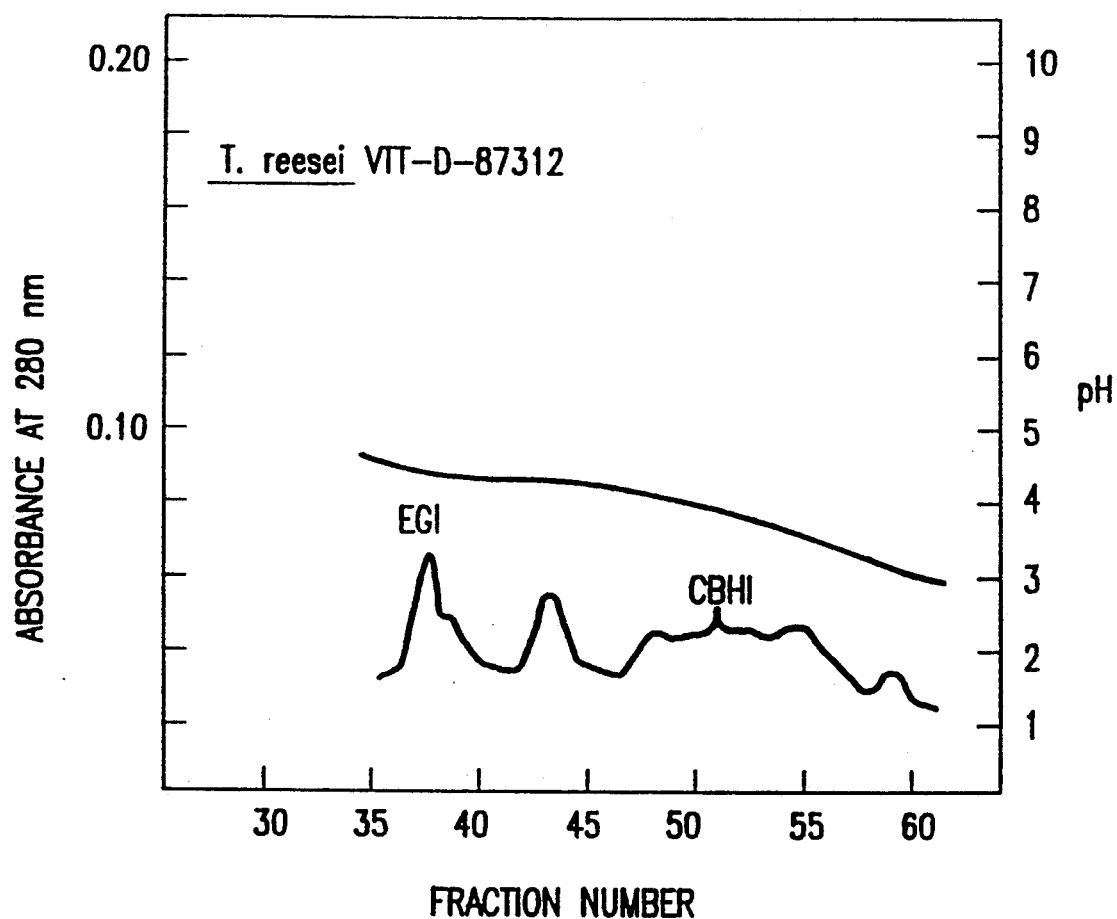

A number of strains produced no detectable CBHI. The CBHI negative character of one of these strains VTT-D-87312 was confirmed by analyzing the growth medium in SDS-PAGE and in FPLC, in which no peak corresponding CBH1 was seen (FIG. 2). The amount of total secreted protein of the CBHI negative strain was about half of that secreted by the *T. reesei* VTT-D-79125. The filter paper degrading activity, FPU (Mandels et al., "Measurement of Saccharifying Cellulase," in: *Biotechnol. Bioeng. Symp.* no. 6., p. 21–33, Gaden, E.L., Mandels, M.H., Reese, E.T., and Spano, L.A. (eds.), John Wiley and Sons, New York, 1976) activity detected in the culture supernatant fraction of the strain VTT-D-87312 was significantly reduced and was about 20% of normal. The lack of the major cellobiohydrolase which normally represents about 60% of the total secreted protein did not notably change the growth properties of the strain.

B. Deletion of the cbh2 Gene with Its Promoter

Figure 3:
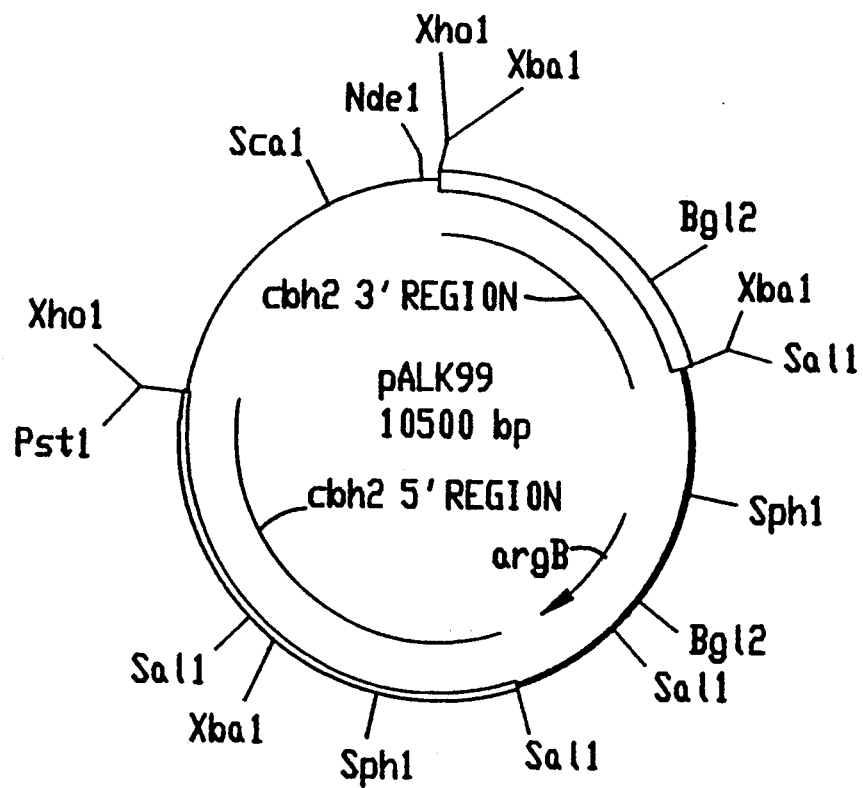
FIG. 3 shows a diagram of the plasmid pALK99.
Figure 4:
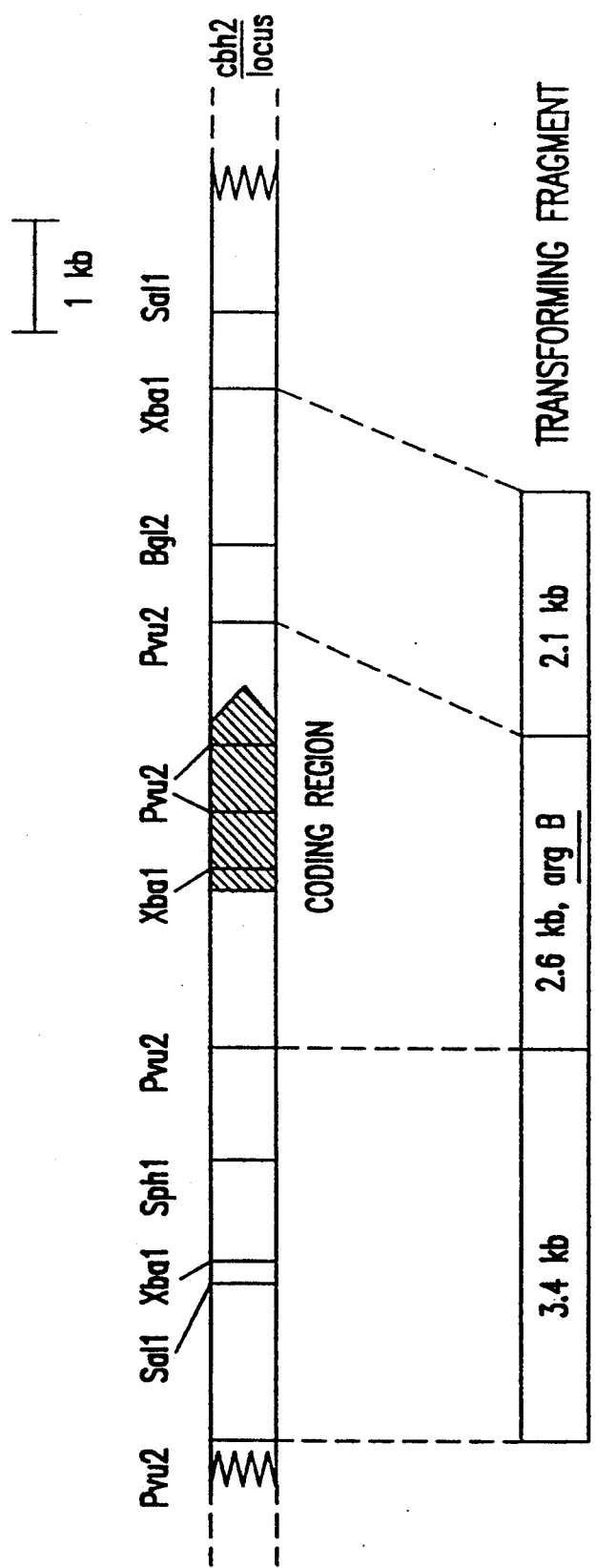
FIG. 4 shows a diagram of the replacement of the chromosomal cbh2 gene with the argB gene.

The cbh2 gene of Trichoderma was replaced with the Aspergillus argB gene as described below. Plasmid pALK99 was constructed to be the source of the transforming fragment (FIG. 3). Plasmid pALK99 was constructed in the following way. The PvuII fragment (containing the multilinker) of the plasmid pUC19 was replaced by a new synthetic multilinker fragment containing recognition sites for the following restriction enzymes: XhoI-StuI-SmaI-XbaI-PvuII-SalI-XhoI. The new plasmid was called pALK96. This plasmid was cut with XbaI and PvuII and a 2.1 kb XbaI-PvuII fragment from the 3' region of the cbh2 gene (see FIG. 4) was ligated into it. The resulting plasmid was cut with PvuII and HincII and ligated with the 3.4 kb PvuII-fragment from the 5' area of the cbh2-gene (see FIG. 4). Both the 3' and 5' fragments were originally from the λ clone cbh2lambda1 (Teeri et al., Gene 51:43–52 (1987)). The resulting plasmid was called pALK98. The Aspergillus nidulans argB gene (2.6 kb SalI fragment) was then ligated between the 3' and 5' regions of the cbh2 gene into the unique PvuII site of plasmid pALK98. The resulting plasmid was called pALK99. Thus, the transforming fragment which is isolated from pALK99 as a XhoI fragment contains the Aspergillus argB gene as a 2.6 kb SAII fragment (Berse et. al., Gene 25:109–117 (1983)) between 3.4 kb (PvuII-PvuII fragment) of the 5' flanking region and 2.1 kb (PvuII-XbaI fragment) of the 3' flanking region of the cbh2 gene (see FIG. 4). *T. reesei* VTT-D-87305 ArgB⁻ mutant strain (Penttila et al., 1987, Gene 61:155–164) was transformed with this fragment using selection for arginine prototropy. ArgB+ transformants were then screened for CBHII⁻ phenotype by Western blotting using monoclonal antibody against CBHII. Replacement of the cbh2 locus by the transforming fragment was then confirmed by Southern blots. Strain Alko 2564 is an example of this kind of "replacement" strain and thus does not contain the cbh2 gene any more.

EXAMPLE 2

Construction of a CBHI Negative Trichoderma Strain Producing Elevated Amounts of EGI The CBHI negative strain VTT-D-87312 described in Example 1A was transformed with the plasmid PAMH 111 to enhance EGI expression in a CBHI negative background. The plasmid pAMH 111 was constructed using the general expression vector pAMH 110 (both of these plasmids are described in EP 244,234). pAMH 110 was built from pUC19 (Janesch Perron et al., Gene 33:103–119 (1985)). First the single NdeI site of pUC19 was destroyed by filling in the recessed ends with Klenow polymerase, and then the plasmid was digested with EcoRI and PstI and ligated to cbh1 promoter and terminator fragments to make an expression cassette. The promoter fragment was a 2.6 kb EcoRI-PstI fragment from the plasmid PAMH 102 (Harkki et al., *Bio/Technology* 7:596–603 (1989)). The terminator was a 0.75 kb AvaII fragment contained in a PstI fragment which also included an adaptor with the TAA stop codon in all three reading frames. pAMH 110 was then digested with SacII and NdeI to remove a piece of DNA between the cbh1 promoter and terminator, and the digested ends were made blunt-ended with $S_1$ nuclease and Klenow polymerase. The egl1 CDNA to be expressed was taken from the plasmid pTTc11 ((Teeri et al., *Anal. Biochem.* 164:60–67 (1987); Penttili et al., *Yeast* 3:175–185 (1987)) as a 1.6 kb EcoRI-BamHI fragment, made bluntended with Klenow polymerase, and ligated into the expression cassette to give plasmid pAMH 111. Transformation was carried out as a co-transformation with pAMH111 and the plasmid pAN8-1 (Mattern et.al., "Transformations of *Aspergillus oryzae*," In: *Abstracts of the 19th Lunteren Lectures of Molecular Genetics of Yeasts and Filamentous Fungi and its Impact on Biotechnology*, Lunteren, the Netherlands, p.34, (1987) carrying the phleomycin resistance gene of *Steptoallotheicus hindustanus* under the *A. nidulans* gpd promoter. Another marker must be used if, as in this example, strain VTT-D-87312 was already AmdS+. Transformants were purified and tested for endoglucanase production in shake flasks cultures. In about 20% of the transformants, the level of hydroxyethylcellulose (HEC) hydrolyzing activity was higher than in the recipient strain. The amount of EGI protein (Table 1) in the shake culture supernatant fraction was analyzed from three transformants showing high HEC activity. Southern blot analysis of these transformants showed that in the best endoglucanase producing clone (Alko 2466) the expression cassette containing the egl1 cDNA between the cbh1 promoter and terminator sequences was integrated in the chromosomal cbh1 locus through the terminator sequences on the insert. The amount of secreted EGI protein in this transformant strain (Alko 2466) was increased about four fold over that of the control (Table 1).

TABLE 1

Characterization of EGI production in *T. reesei* VTT-D-87312 (CBHI negative transformant of VTT-D-79125) and in Alko 2493, Alko 2466 and Alko 2498 which arise from VTT-D-87312 transformed with the plasmid pAMH111. VTT-D-79125 is the untransformed high-cellulase producing *T. reesei* mutant strain. All strains were grown in shake flasks as described in the Materials and Methods. The amount of EGI protein and total secreted protein were measured after 7 days cultivation as described in the Materials and Methods.

|  | EGI protein (mg/ml) | Total secreted protein (mg/ml) | % EGI % of the total secreted protein |
|---|---|---|---|
| VTT-D-87312 | 0.35 | 4.5 | 7.7 |
| Alko 2493 | 1.25 | 5.2 | 24.0 |
| Alko 2466 | 1.90 | 5.8 | 32.8 |
| Alko 2498 | 1.40 | 5.9 | 23.7 |
| VTT-D-79125 | 0.75 | 10.6 | 7.1 |

EXAMPLE 3

Figure 5:
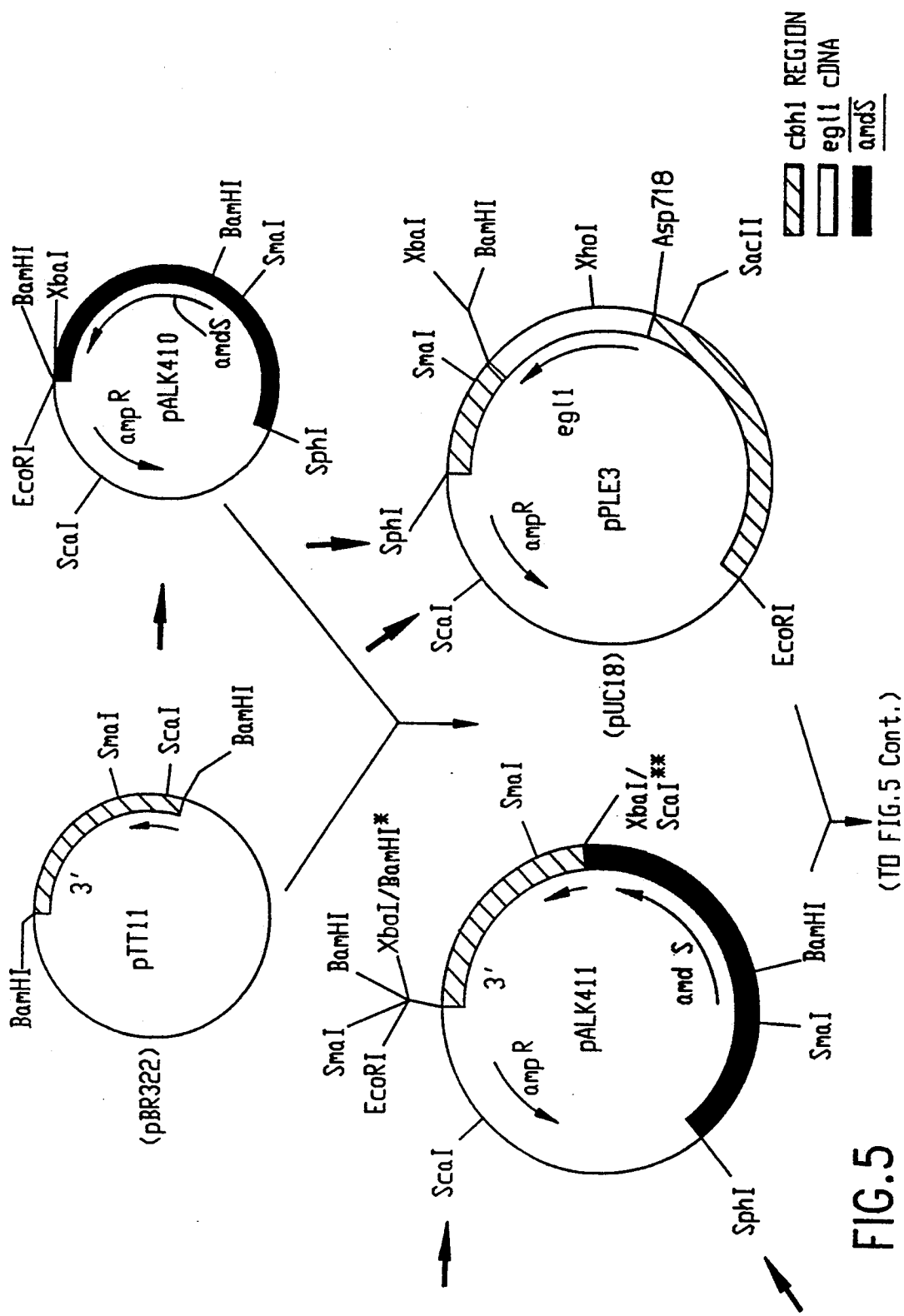
FIG. 5 shows the construction of the plasmid pALK412.
Figure 5:
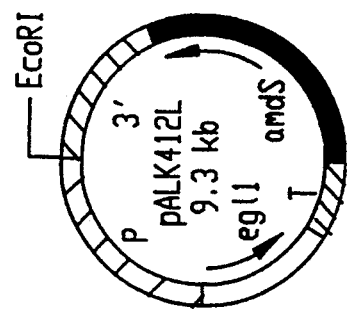
Figure 5:
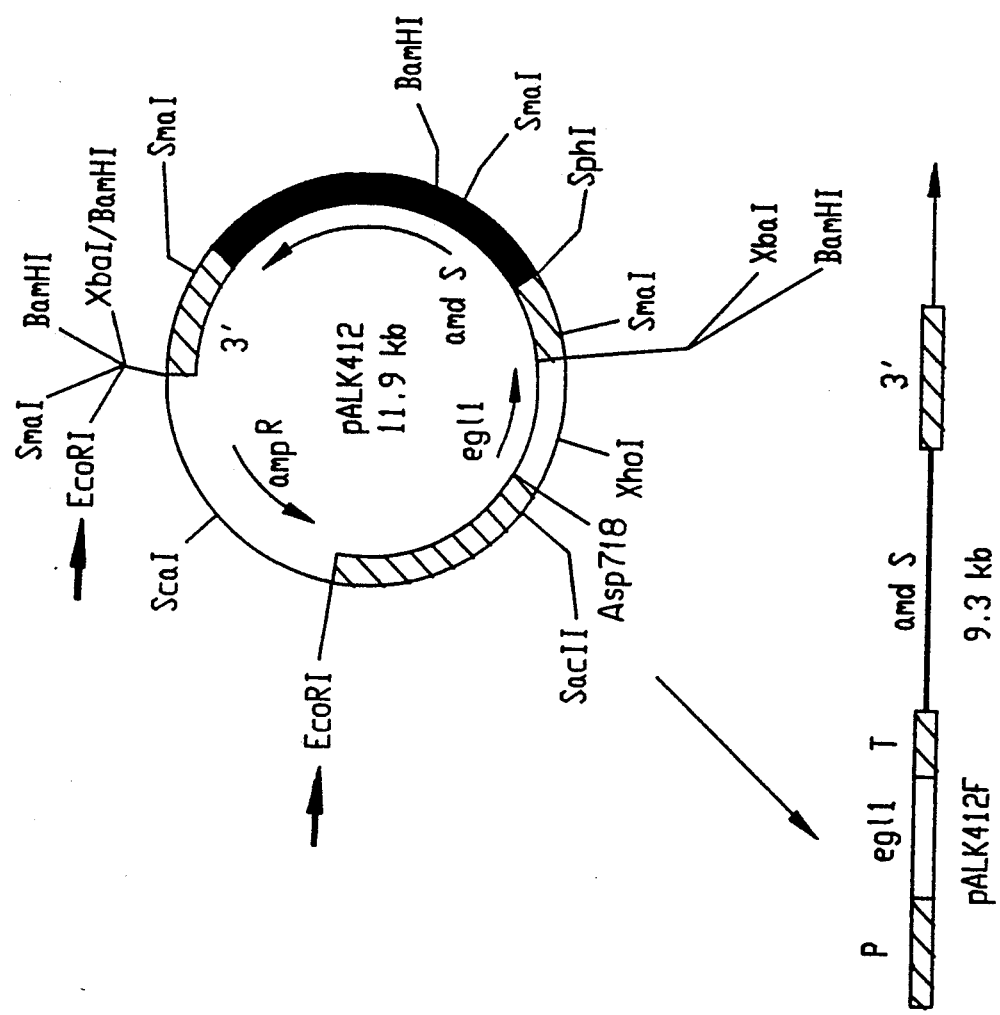

Simultaneous Inactivation of the cbh1 Gene and Multiplication of the egl1 Copy Number The cbh1 gene of *T.reesei* VTT-D-79125 was replaced with the Trichoderma egl1 cDNA and amds gene. The egl1 cDNA was ligated between the promoter and terminator of cbh1 gene. Plasmid pALK412 was constructed to be the source of the transforming fragment. The plasmid pALK412 was prepared as in FIG. 5.

The plasmid p3SR2 which contains the *Aspergillus nidulans* amdS gene cloned into pBR322 (Kelly and Hynes, *EMBO J.* 4:475–479 (1985)) was digested with SphI and with XbaI. The resulting 3.2 kb DNA fragment bearing the whole amdS gene was ligated to the SphI and XbaI cut pUC19 vector (Yanisch-Perron et al., *Gene* 33:103–119 (1985)). The resulting plasmid was called pALK410.

A DNA fragment containing 1.65 kb of the 3' region of the cbh1 gene starting from the ScaI site in the coding region was isolated as a ScaI-BamHI fragment and blunt-ended with Klenow-enzyme. This fragment was ligated to the XbaI site (blunt-ended with Klenow enzyme) of the plasmid pALK410. In this case the 3' fragment was isolated from the plasmid pTT11. Plasmid pTT11 (Teeri et al., *Bio/Tech* 1:696–699 (1983)) contains 1.8 kb fragment of the cbh1 region, 3' from the BamHI site in the coding region, cloned into the BamHI site of pBR322. The gene can also be isolated from other sources, for example, from a λ clone 44A (Teeri et al., *Bio/Tech* 1:696–699).

Figure 6:
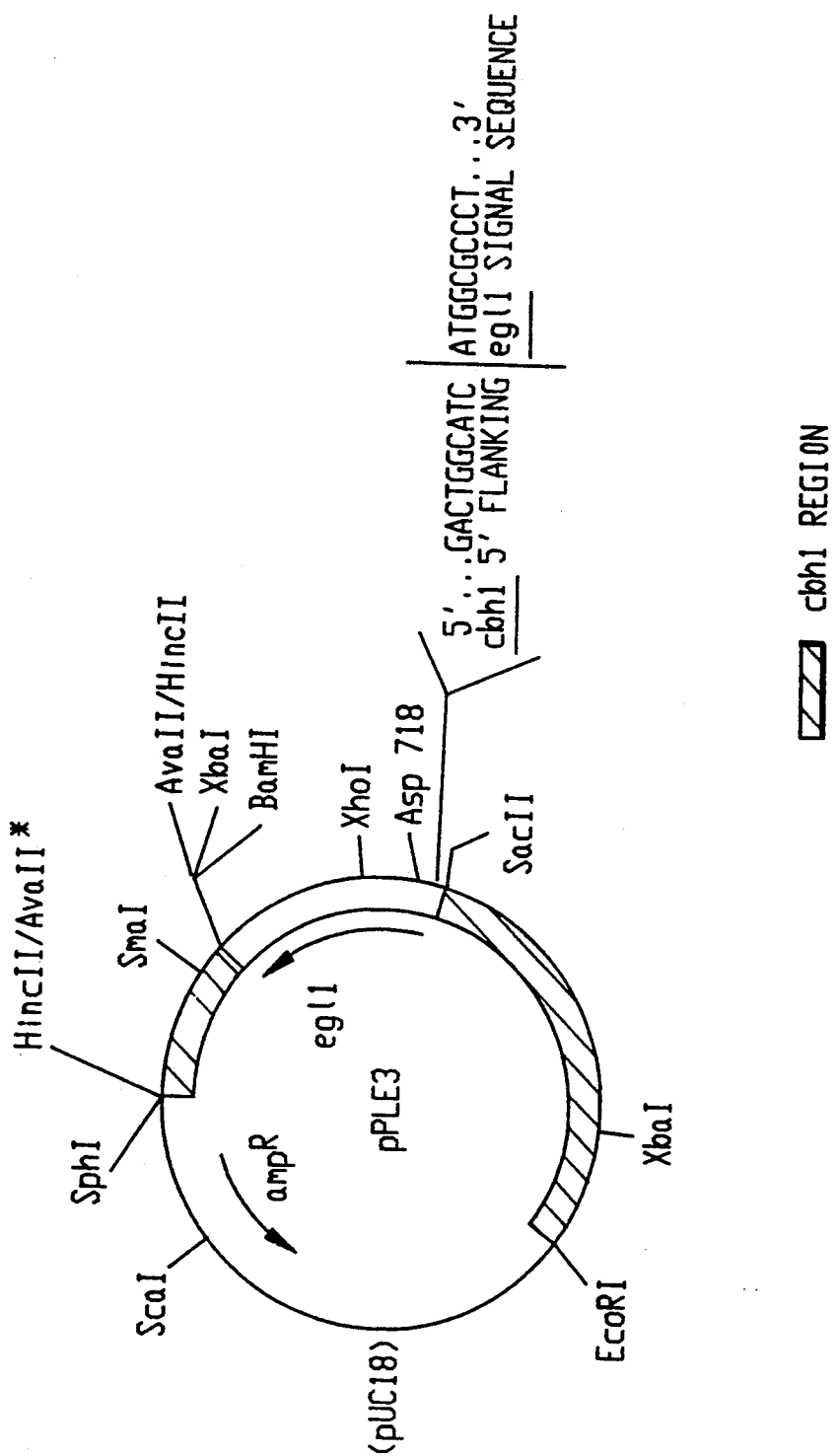
FIG. 6 shows a diagram of plasmid pPLE3.

The plasmid obtained was pALK411. It was digested with ScaI and with SphI. The 5.8 kb fragment was ligated to ScaI and SphI cut plasmid pPLE3 (Nevalainen, et al., In: *Molecular Industrial Mycology: Systems and Applications for Filamentous Fungi*, Leong et al., eds., pp. 129–148 (1990)) which contains egl1 cDNA between the promoter and terminator regions of cbh1 gene cloned into pUC18 (FIG. 6). The promoter and terminator regions are from the expression vector pAMH110 (Nevalainen et al. In: *Molecular Industrial Mycology: Systems and Applications for Filamentous Fungi*, Leong et al., eds., pp. 129–148 (1990)).

The resulting plasmid pALK412 was cut with EcoRI to remove the bacterial DNA. The 9.3 kb pALK412F fragment was also backligated to form plasmid pALK412L.

*T. reesei* VTT-D-79125 (Bailey and Nevalainen, *Enzyme Microb. Technol.* 3:153–157 (1981)) was transformed with plasmid pALK412, with pALK412F linear fragment, with backligated pALK412L and with pALK412F and pALK412L at the same time with a molar ratio of 5:1 respectively. Transformants were selected on the basis of the amdS+ phenotype and purified from conidia on selective medium containing acetamide as a sole nitrogen source.

Purified transformants were grown on microtiter plates and were screened for CBHI− phenotype by Western blotting using polyclonal antibody against CBHI protein. About one third of the pALK412F transformants produced no detectable CBHI. There was one CBHI− transformant among forty strains that had transformed with the plasmid pALK412.

CBHI− transformants were tested for endoglucanase production in shake flasks cultures. In all of these transformants the level of hydroxyethylcellulose (HEC) hydrolyzing activity was higher than in the recipient strain. The best transformants secreted 4–5 times the endoglucanase activity of the recipient strain.

Southern blot analysis of the CBHI transformants showed that their cbh1 locus was replaced by the vector fragment. The chromosomal DNA of the transformants was digested with XhoI and hybridized with the 0.5 kb fragment of the cbh1 coding region probe.

The best endoglucanase producing strains had more than one copy of the vector fragment which carries the gene of interest inserted into the Trichoderma genome.

EXAMPLE 4

Use of the Enzyme Preparations in Biobleaching

A novel Trichoderma enzyme preparation which contains no cellobiohydrolase I activity (CBHI−) and in which the xylanase fraction is thus enriched, was used to biobleach pulp during wood processing. Approximately one liter of concentrated culture medium as described above per ton of pulp was added pine kraft pulp. The culture medium may be ultrafiltered by techniques well known in the art or concentrated as using techniques well known in the art, to achieve a desired concentration of protein or enzyme activity. The results indicated that the kappa number (the amount of lignin) of pine kraft pulp was lowered by this treatment without affecting the mechanical properties of the pulp. If the enzyme treated pulp was chemically bleached, the chlorine consumption was significantly decreased.

Having now fully described the invention, it will be understood by those with skill in the art that the scope may be performed within a wide and equivalent range of conditions, parameters and the like, without affecting the spirit or scope of the invention or any embodiment thereof. All references cited herein are fully incorporated herein by reference.

What is claimed is:

1. A method for producing an enzyme preparation in a culture medium, said method comprising the steps of:
    (a) modifying a Trichoderma host cell such that said host cell is partially or completely deficient in expressing one or more endogenous cellulase enzymes;
    (b) transforming the host cell of part (a) with a genetic construct comprising a nucleotide sequence encoding a protein selected from the group consisting of a hemicellulase, a pectin degrading enzyme, a lignin degrading enzyme other than lignin peroxidase LIII of P. radiata, and a cellulolytic enzyme, wherein the transformation inserts said nucleotide sequence into the chromosome of said host cell;
    (c) screening said host cell of part (b) and identifying a host cell which expresses said protein;
    (d) cultivating said transformed Trichoderma host cell of part (c) under conditions which allow the expression of said protein; and
    (e) recovering the culture medium from the cultivation of part (d), wherein said culture medium contains said protein and the enzymes secreted by said transformed Trichoderma host cell during the cultivation of part (d).

2. A method according to claim 1, wherein said Trichoderma host cell of step is deficient in a cellulase enzyme selected from the group consisting of cellobiohydrolase I, cellobiohydrolase II, endoglucanase I and endoglucanase II.

3. A method according to claim 2, wherein said cellulase enzyme is cellobiohydrolase I.

4. A method according to claim 1, wherein said Trichoderma host according to part (b) contains more than one copy of said nucleotise sequence encoding said protein.

5. A method according to claim 1, wherein said Trichoderma host according to part (b) is transformed to contain at least one copy of said nucleotide sequence encoding said protein integrated into the cbh1 locus of said Trichoderma host cell.

6. A method according to claim 1, wherein said cellulolytic enzyme is endoglucanase I.

7. A transformed Trichoderma host cell, wherein said transformed Trichoderma host cell is modified such that said host cell is partially or completely deficient in expressing one or more endogenous cellulase enzymes and wherein said transformed Trichoderma host cell has been transformed with a genetic construct comprising a nucleotide sequence encoding a protein selected from the group consisting of a hemicellulase, a pectin degrading enzyme, a lignin degrading enzyme other than lignin peroxidase LIII of P. radiata, and a cellulolytic enzyme, and wherein said nucleotide sequence encoding said protein has been integrated into the genome of said transformed Trichoderma host cell.

8. The host cell of claim 7 or claim 1, wherein said cellulase enzyme in which said Trichoderma is partially or completely deficient is selected from the group consisting of cellobiohydrolase I, cellobiohydrolase II, endoglucanase I and endoglucanase II.

9. The host cell of claim 8, wherein said cellulase enzyme is cellobiohydrolase I.

10. The host cell of claim 7, wherein said transformed Trichoderma host cell contains more than one copy of said nucleotide sequence encoding said protein.

11. The host cell of claim 7, wherein said Trichoderma host is transformed to contain at least one copy of said nucleotide sequence encoding said protein integrated into the cbh1 locus of said Trichoderma host cell.

12. The host cell of claim 7, wherein said cellulolytic enzyme is endoglucanase I.

13. A method for producing an enzyme preparation deficient in an endogenous Trichoderma cellulase in a culture medium, said method comprising the steps of:
    (a) transforming a Trichoderma host cell, wherein said transformation results in a host cell that is partially or completely deficient in expressing one or more endogenous cellulase enzymes;
    (b) cultivating said transformed Trichoderma host cell;
    (c) recovering the culture medium after said cultivation of part (b), said culture medium containing the enzymes secreted by said Trichoderma host cell during said cultivation; and
    (d) preparing said enzyme preparation from the culture medium recovered in part (c).

14. A transformed Trichoderma host cell, wherein said transformed Trichoderma host cell is modified such that said host cell is partially or completely deficient in expressing one or more endogenous cellulase enzymes and wherein said transformed Trichoderma host cell is capable of expressing one or more endogenous enzymes selected from the group consisting of a hemicellulase, a pectin degrading enzyme, and a cellulolytic enzyme.

15. The culture medium of the transformed Trichoderma host cell of claim 7, comprising the enzymes secreted into the culture medium during culture of said transformed Trichoderma host cell.

16. The culture medium of the transformed Trichoderma host cell of claim 14, comprising the enzymes secreted into the culture medium during culture of said transformed Trichoderma host cell.

17. The culture medium of claim 15 or 16, wherein said Trichoderma has been transformed with a gene encoding an enzyme that is homologous to said Trichoderma.

18. The culture medium of claim 17, wherein said gene encoding said homologous enzyme is selected from the group consisting of a gene encoding a homologous cellulolytic enzyme, a homologous hemicellulase, and a homologous pectin degrading enzyme.

19. The culture medium of claim 15 or 16, wherein said Trichoderma has been transformed with a gene encoding an enzyme that is heterologous to said Trichoderma.

20. The culture medium of claim 19, wherein said gene is selected from the group consisting of a gene encoding a heterologous cellulolytic enzyme, a heterologous hemicellulase, a pectin degrading enzyme and a lignin degrading enzyme other than lignin peroxidase LIII of P. radiata.

21. The culture medium of claim 15, wherein said Trichoderma host cell has been transformed to contain more than one copy of the nucleotide sequence encoding said protein.

22. The culture medium of claim 21, wherein said nucleotide sequence is integrated into the cbh1 locus of said Trichoderma host cell.

23. The culture medium of claim 15 or 16, wherein said Trichoderma host cell is incapable of expressing one or more cellulase enzyme(s) as a result of deleting genomic sequences which encode expression of said cellulase enzyme.

24. The culture medium of claim 23, wherein said deleted genomic sequence is that of a cellulase enzyme selected from the group consisting of cellobiohydrolase I, cellobiohydrolase II, endoglucanase I and endoglucanase II.

25. The culture medium of claim 24, wherein said cellulase enzyme is cellobiohydrolase I.

26. The culture medium of the transformed Trichoderma host cell of claim 7 or 14, wherein said transformation of said Trichoderma host cell results in said partial or complete deficiency in expressing one or more cellulase enzyme(s).

27. The culture medium of claim 26, wherein said cellulase enzyme is selected from the group consisting of cellobiohydrolase I, cellobiohydrolases II, endoglucanase I and endogoucanase II.

28. The culture medium of claim 27, wherein said cellulase enzyme is cellobiohydrolase I.

29. The culture medium of claim 15 or 16, wherein said Trichoderma has been transformed with a genetic construct comprising a nucleotide sequence encoding a cellulolytic enzyme.

30. The culture medium of claim 29, wherein said cellulolytic enzyme is selected from the group consisting of cellobiohydrolase I, cellobiohydrolase II, endoglucanase I and endoglucanase II.

31. The culture medium of claim 30, wherein said cellulolytic enzyme is endoglucanase I.

* * * * *

UNITED STATES PATENT AND TRADEMARK OFFICE
CERTIFICATE OF CORRECTION

PATENT NO. : 5,298,405
DATED : March 29, 1994
INVENTOR(S) : NEVALAINEN et al.

It is certified that error appears in the above-indentified patent and that said Letters Patent is hereby corrected as shown below:

On the title page, in item 54, line 2, delete "CELLULOSE" and insert therein --CELLULASE--.

On the title page, in item 75, line 3, delete "Pentillä" and insert therein --Penttila--.

On the title page, between the filing date [22] and the Related U.S. Application Data [63], insert --[30] Foreign Application Priority Data Apr. 30, 1986 [UK] United Kingdom ... 8610600--.

On the title page, column 2, under the heading "Other Publications," line 4, delete "PenttiläM."; and insert therein --Penttilä, M.--; line 19, delete "1987" and insert therein --1988--; in the Abstract, line 5, delete, "an", and insert therein --a--.

Page 2, column 1, under the heading "Other Publications," line 17, delete "559", and insert therein --599--; line 26, delete "Doe", and insert therein --the--; line 28, delete "Nevalanen", and insert therein --Nevalainen--; line 31, delete "Nevalainca" and insert therein, --Nevalainen--.

UNITED STATES PATENT AND TRADEMARK OFFICE
CERTIFICATE OF CORRECTION

PATENT NO. : 5,298,405
DATED : March 29, 1994
INVENTOR(S) : NEVALAINEN et al.

Page 2 of 7

It is certified that error appears in the above-indentified patent and that said Letters Patent is hereby corrected as shown below:

Sheet 7 of the Drawings, delete (Fig. 5 cont.), and replace with the following:

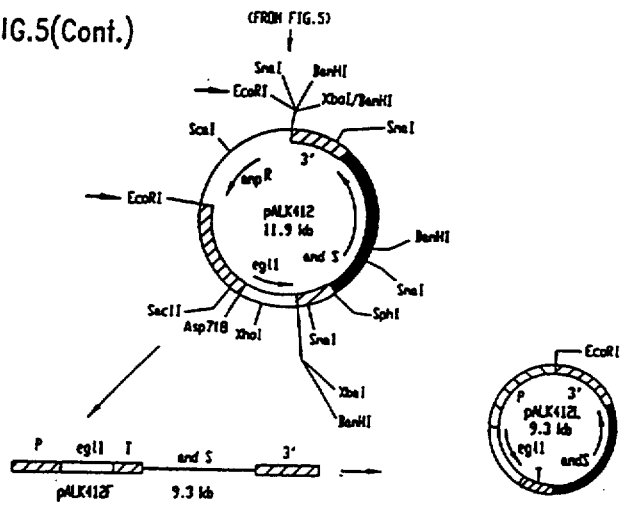

UNITED STATES PATENT AND TRADEMARK OFFICE
CERTIFICATE OF CORRECTION

PATENT NO. : 5,298,405
DATED : March 29, 1994
INVENTOR(S) : NEVALAINEN et al.

Page 3 of 7

It is certified that error appears in the above-indentified patent and that said Letters Patent is hereby corrected as shown below:

Sheet 6 of the Drawings, delete (Fig. 5), and replace with the following:

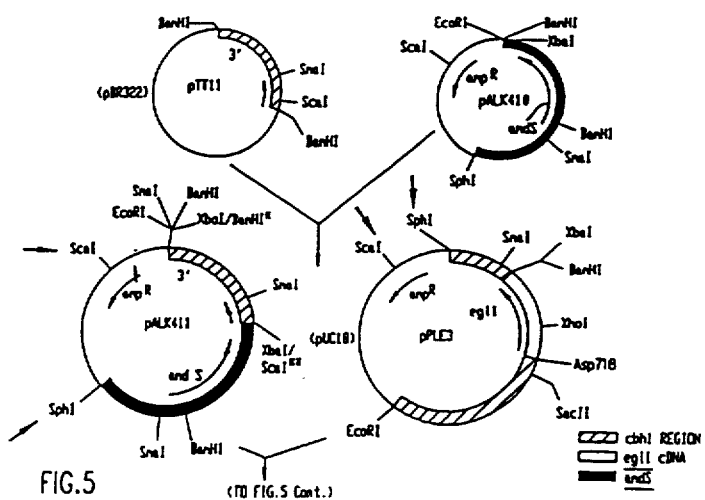

FIG.5

UNITED STATES PATENT AND TRADEMARK OFFICE
CERTIFICATE OF CORRECTION

PATENT NO. : 5,298,405
DATED : March 29, 1994
INVENTOR(S) : NEVALAINEN et al.

It is certified that error appears in the above-indentified patent and that said Letters Patent is hereby corrected as shown below:

Page 2, column 2, under the heading "Other Publications," line 3, delete "Kemiu-Kemi" and insert therein --Kemia-Kemi--; line 7, delete "Bio Chemistry" and insert therein --Biochemistry--; line 10, delete "Poutaneva" and insert therein --Poutanen--; line 13, delete "Pentillä", and insert therein --Penttilä--; line 16, delete "El-Gregory", and insert therein --El-Gogory--; line 29, delete "*Celluloses*", and insert therein --*Cellulases*--.

Column 1, line 2 in the title of the invention, delete "CELLULOSE", and insert therein --CELLULASE--.

Column 2, line 56, delete "shows", and insert therein --show--.

Column 3, line 2, delete "(RDNA)", and insert therein --(rDNA)--.

Column 6, line 28, delete "mutengenizing", and insert therein --mutagenizing--; line 66, delete "eg11, eg13" and insert therein --egl1, egl3--.

Column 7, line 30, delete "1acZ", and insert therein --lacZ--.

Column 8, line 5, delete "696", and insert therein --695--; line 10, insert --(1987)-- between "5:60-64" and ")"; line 12, delete "eg13" and insert therein --egl3--.

UNITED STATES PATENT AND TRADEMARK OFFICE
CERTIFICATE OF CORRECTION

PATENT NO. : 5,298,405
DATED : March 29, 1994
INVENTOR(S) : NEVALAINEN et al.

It is certified that error appears in the above-indentified patent and that said Letters Patent is hereby corrected as shown below:

Column 10, line 16, delete "pAMHI10", and insert therein --pAMH110--; line 17, delete "Janisch", and insert therein --Yanisch-; line 22, delete "Sac1I", and insert therein --SacII--.

Column 11, line 51, delete "a".

Column 13, line 24, delete "$^{32}$p", and insert therein --$^{32}$P--.

Column 15, line 31, delete "forms", and insert therein --form--.

Column 19, line 26, delete the comma "," and insert therein a period --.--; line 41, delete "1987" and insert therein, --1988--.

Column 20, line 47, delete "were", and insert therein --where--; line 62, delete "Diagnostics", and insert therein --Diagnostica--; and line 65, delete "NAOH", and insert therein --NaOH--.

Column 21, line 2, delete "endolgucanase", and insert therein --endoglucanase--; line 22, delete "Cellulose" and insert therein --Cellulase--; and line 38, delete "Janesch" and insert therein --Yanisch--; line 61, delete "CBH1" and insert therein --CBHI--.

UNITED STATES PATENT AND TRADEMARK OFFICE
CERTIFICATE OF CORRECTION

PATENT NO. : 5,298,405

DATED : March 29, 1994

INVENTOR(S) : NEVALAINEN *et al.*

Page 6 of 7

It is certified that error appears in the above-indentified patent and that said Letters Patent is hereby corrected as shown below:

Column 22, line 17, delete "Pvul1", and insert therein --PvuII--; line 21, delete "PvuI", and insert therein --PvuII--; line 22, delete "Hinc1I", and insert therein --HincII--; line 33, delete "SAII", and insert therein --SalI--; line 33, delete "et. al.,", and insert therein --et al.,--; line 35, delete "Pvul1", and insert therein --PvuII--; line 37, delete "Penttila" and insert therein --Penttilä--; line 52, delete "PAMH" and insert therein --pAMH--.

Column 22, line 58, delete "Janesch", and insert therein --Yanisch--; and line 65, delete "PAMH", and insert therein --pAMH--.

Column 23, line 5, delete "CDNA", and insert therein --cDNA--; line 7, delete "Penttili", and insert therein --Penttilä--; line 8, delete "Yeast", and insert therein --*Yeast*--; line 11, delete "pAMH 111" and insert therein --pAMH111--; line 47, delete "EGl", and insert therein --EGI--; and line 61, delete "amds", and insert therein --amdS--.

Column 24, line 8, delete "ScaI-BamHl", and insert therein --ScaI-BamHI--; and line 26, delete "cbhl", and insert therein --cbh1--.

UNITED STATES PATENT AND TRADEMARK OFFICE
CERTIFICATE OF CORRECTION

PATENT NO. : 5,298,405
DATED : March 29, 1994
INVENTOR(S) : NEVALAINEN et al.

It is certified that error appears in the above-indentified patent and that said Letters Patent is hereby corrected as shown below:

Column 25, line 9, add --to-- between the words "added" and "pine"; line 11, delete "as" between the words "concentrated" and "using"; line 53, (Claim 2, line 1), after "1" insert --or claim 13-; line 54, (Claim 2, line 2), insert --(a)-- between the words "step" and "is"; line 62, claim 4, delete "nucleotise", and insert therein --nucleotide--.

Column 26, line 16 (Claim 8, line 1), delete "1" and insert therein --14--; line 27, (Claim 11, line 2), insert --cell-- between the words "host" and "is".

Signed and Sealed this

Thirty-first Day of January, 1995

Attest:

BRUCE LEHMAN

Attesting Officer        Commissioner of Patents and Trademarks